(12) United States Patent
Youngs et al.

(10) Patent No.: US 8,648,064 B2
(45) Date of Patent: Feb. 11, 2014

(54) METAL COMPLEXES OF N-HETEROCYCLIC CARBENES

(75) Inventors: Wiley J. Youngs, Akron, OH (US);
Matthew J. Panzner, Akron, OH (US);
Carolyn L. Cannon, Coppell, TX (US)

(73) Assignee: The University of Akron, Akron, OH (US)

( * ) Notice: Subject to any disclaimer, the term of this patent is extended or adjusted under 35 U.S.C. 154(b) by 591 days.

(21) Appl. No.: 12/902,807

(22) Filed: Oct. 12, 2010

(65) Prior Publication Data

US 2011/0086830 A1    Apr. 14, 2011

Related U.S. Application Data

(63) Continuation-in-part of application No. 11/482,410, filed on Jul. 7, 2006, now Pat. No. 8,519,146, which is a continuation-in-part of application No. 10/569,563, filed as application No. PCT/US2004/029285 on Sep. 7, 2004, now abandoned.

(60) Provisional application No. 61/250,795, filed on Oct. 12, 2009, provisional application No. 60/500,737, filed on Sep. 5, 2003.

(51) Int. Cl.
*A61K 31/555* (2006.01)
(52) U.S. Cl.
USPC ............ 514/184; 514/186; 544/225; 548/103
(58) Field of Classification Search
USPC ................................................. 514/184, 186
See application file for complete search history.

(56) References Cited

U.S. PATENT DOCUMENTS

2007/0021401 A1    1/2007    Youngs et al.

OTHER PUBLICATIONS

Davis, Jr., et al., "Azolidene Carbenes Derived from Biologically Relevant Molecules, 1 Synthesis and Characterization of Iridium Complexes of Imidazolidene Ligands Based upon the Antifungal Drugs Econazole and Miconazole", Inorg. Chem. 37, pp. 5412-5413, 1998, p. 5412.
Sultana, et al., "Synthesis and Anibacterial Activity of Cephradine Metal Complexes: Part II Complexes with Cobalt, Copper, Zinc and Cadmium", Pakistan Journal of Pharmaceutical Sciences, vol. 18(1), pp. 36-42, Jan. 2005, Abstract; p. 37, p. 40.

*Primary Examiner* — Jeffrey S. Lundgren
*Assistant Examiner* — Sara E Townsley
(74) *Attorney, Agent, or Firm* — Renner Kenner Greive Bobak Taylor & Weber

(57) ABSTRACT

The present invention generally relates to metal complexes of N-heterocyclic carbenes that contain one or more additional active moieties and/or groups therein. In one embodiment, the present invention relates to metal complexes of N-heterocyclic carbenes that contain an anti-fungal and/or anti-microbial moiety and/or group in combination with one or more additional active moieties and/or groups selected from fluoroquinolone compounds or derivatives thereof; steroids or derivatives thereof; anti-inflammatory compounds or derivatives thereof; anti-fungal compounds or derivatives thereof; anti-bacterial compounds or derivatives thereof; antagonist compounds or derivatives thereof; $H_2$ receptor compounds or derivatives thereof; chemotherapy compounds or derivatives thereof; tumor suppressor compounds or derivatives thereof; or $C_1$ to $C_{16}$ alkyl heteroatom groups where the heterotatom is selected from S, O, or N. In still another embodiment, the present invention relates to metal complexes of N-heterocyclic carbenes that contain an anti-fungal and/or anti-microbial moiety and/or group in combination with two or more additional active moieties and/or groups selected from fluoroquinolone compounds or derivatives thereof; steroids or derivatives thereof; anti-inflammatory compounds or derivatives thereof; anti-fungal compounds or derivatives thereof; anti-bacterial compounds or derivatives thereof; antagonist compounds or derivatives thereof; $H_2$ receptor compounds or derivatives thereof; chemotherapy compounds or derivatives thereof; tumor suppressor compounds or derivatives thereof; or $C_1$ to $C_{16}$ alkyl heteroatom groups where the heterotatom is selected from S, O, or N.

1 Claim, 17 Drawing Sheets

METAL COMPLEXES OF N-HETEROCYCLIC CARBENES

RELATED APPLICATION DATA

This application is a continuation-in-part of U.S. patent application Ser. No. 11/482,410, filed on Jul. 7, 2006, which is a continuation-in-part application of U.S. patent application Ser. No. 10/569,563, filed on Nov. 13, 2006, which is a 35 U.S.C. §371 application of International Application No. PCT/US2004/029285, filed on Sep. 7, 2004, which claims priority to U.S. Provisional Patent Application No. 60/500,737, filed on Sep. 5, 2003. Additionally, this application claims priority to U.S. Provisional Patent Application No. 61/250,795, filed on Oct. 12, 2009, and entitled "Metal Complexes of N-Heterocyclic Carbenes." All of these patent applications are incorporated herein in their entireties by reference.

The present invention was made in the course of research that was supported by Award Number NIH R15 CA 96739-01; and Award Number NSF CHE-0116041. The United States government may have certain rights to the invention or inventions herein.

FIELD OF THE INVENTION

The present invention generally relates to metal complexes of N-heterocyclic carbenes that contain one or more additional active moieties and/or groups therein. In one embodiment, the present invention relates to metal complexes of N-heterocyclic carbenes that contain an anti-fungal and/or anti-microbial moiety and/or group in combination with one or more additional active moieties and/or groups selected from fluoroquinolone compounds or derivatives thereof; steroids or derivatives thereof; anti-inflammatory compounds or derivatives thereof; anti-fungal compounds or derivatives thereof; anti-bacterial compounds or derivatives thereof; antagonist compounds or derivatives thereof; $H_2$ receptor compounds or derivatives thereof; chemotherapy compounds or derivatives thereof; tumor suppressor compounds or derivatives thereof; or $C_1$ to $C_{16}$ alkyl heteroatom groups where the heteroatom is selected from S, O, or N. In still another embodiment, the present invention relates to metal complexes of N-heterocyclic carbenes that contain an anti-fungal and/or anti-microbial moiety and/or group in combination with two or more additional active moieties and/or groups selected from fluoroquinolone compounds or derivatives thereof; steroids or derivatives thereof; anti-inflammatory compounds or derivatives thereof; anti-fungal compounds or derivatives thereof; anti-bacterial compounds or derivatives thereof; antagonist compounds or derivatives thereof; $H_2$ receptor compounds or derivatives thereof; chemotherapy compounds or derivatives thereof; tumor suppressor compounds or derivatives thereof; or $C_1$ to $C_{16}$ alkyl heteroatom groups where the heteroatom is selected from S, O, or N.

BACKGROUND OF THE INVENTION

Silver has long been used for its antimicrobial properties. This usage predates the scientific or medical understanding of its mechanism. For example, the ancient Greeks and Romans used silver coins to maintain the purity of water. Today silver is still used for this same purpose by NASA on its space shuttles. Treatment of a variety of medical conditions using silver nitrate was implemented before 1800. A one percent silver nitrate solution is still widely used today after delivery in infants to prevent gonorrheal ophthalmia. Since at least the later part of the nineteenth century, silver has been applied in a variety of different forms to treat and prevent numerous types of bacteria related afflictions.

Other treatments, such as the application of silver foil to post surgical wounds to prevent infection survived as a medical practice into the 1980's in Europe, and silver nitrate is still used as a topical antimicrobial agent. In the 1960's the very successful burn treatment silver complex, silver sulfadiazine, shown in Formula 1 below, was developed. Commercially known as Silvadene® Cream (one percent) this complex has remained one of the most effective treatments for preventing infection of second and third degree burns. Silver sulfadiazine has been shown to have good antimicrobial properties against a number of gram-positive and gram-negative bacteria. It is believed that the slow release of silver at the area of the superficial wound is responsible for the process of healing. Studies on surgically wounded rats have shown the effectiveness of both silver nitrate and silver sulfadiazine to aid in the healing process. By using these common silver antimicrobial agents, inflammation and granulation of wounds were reduced, although the complete mechanism for these phenomena is not understood.

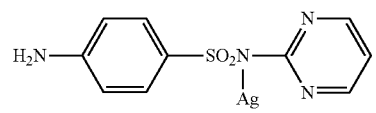

Recently developed silver-coating techniques have lead to the creation of a burn wound dressing called Acticoat. The purpose of this dressing is to avoid adhesion to wounds while providing a barrier against infection. Some clinical trials have also demonstrated the ease of removal of the dressing in contrast to conventional wound dressings treated with silver nitrate. Acticoat has shown an increase in antibacterial function over both silver nitrate and silver sulfadiazine. Acticoat is made up of nanocrystalline silver particles. Antibiotic-resistant strains have developed rarely to both silver nitrate and silver sulfadiazine but not to nanocrystalline silver. The broader range of activity of nanocrystalline silver is apparently due to the release of both silver cations and uncharged silver species. Due to the continuing emergence of antibiotic resistant strains of infectious agents, a need exists for novel antibiotics.

Metal compounds have also played a significant role in other therapeutic applications. One example of the usefulness of the metals can be seen in the field of radiopharmaceuticals. The use of radiation therapy to destroy tumor cells is well known, but tumors can reappear after therapy. Hypoxic cells within the tumor are 2.5 to 3 times more resistant to X-ray radiation than other tumor cells. For this reason, these cells are more likely to survive radiation therapy or chemotherapy and lead to the reappearance of the tumor. Targeting of radio nuclides to hypoxic cells will serve as a method to visualize them.

Complexes of γ-ray emitters such as $^{99}Tc$ are extremely useful as imaging agents, and therapeutic radiopharmaceuticals like $^{89}Sr$, $^{153}Sm$, $^{186}Re$ and $^{166}Ho$ are important in the treatment of bone tumors. bRh-105 emits a gamma ray of 319 keV (19%) that would allow in vivo tracking and dosimetry calculations. Many more radioactive nuclei can be harnessed by using the entire periodic table to construct diagnostic or therapeutic agents.

Urinary tract infections (UTIs) represent the second most common infectious disease in the United States and are associated with substantial morbidity and medical cost. These infections, including cystitis and pyelonephritis, are most commonly caused by uropathogenic *Escherichia coli* (UPEC). Patients with neurogenic bladder, indwelling urinary catheters, or vesicoureteral reflux, as well as otherwise healthy women, experience recurrences; repeated infections of the urinary tract can lead to renal scarring and chronic kidney disease (CKD). Current preventive and therapeutic strategies fail to address the problem of recurrent UTIs. Recent work in the murine cystitis model has unveiled new paradigms regarding the pathogenesis of UTI. Long thought to be strictly extracellular pathogens, UPEC have been shown to invade superficial epithelial cells lining the bladder and to establish large collections, termed intracellular bacterial communities (IBCs), within these cells. From there, UPEC form a quiescent reservoir within bladder tissue that is sequestered from host defenses, resists antibiotic therapies, and can serve as a nidus for recurrence.

The rapid rise in antimicrobial resistance rates among pathogenic strains renders treatment and prophylactic regimens for UTI increasingly difficult. For this reason, it is desired to interrogate the utility of silver carbenes as novel antimicrobials within the urinary tract. The antimicrobial properties of silver have been recognized for centuries, and there is recent resurgence of interest in this metal as a biocide. Though silver-impregnated urinary catheters have reduced the incidence of UTI in certain populations (e.g., patients with indwelling catheters), novel strategies are needed to prevent recurrent UTI in other patients (e.g., healthy women and patients with functional and anatomic abnormalities of the urinary tract). Organometallic complexes of silver with N-heterocyclic carbenes (NHCs), have been designed and synthesized. The primary advantage of these silver carbenes (SCs) over existing silver compounds is their stability and water solubility.

The usefulness of complexes of radioactive metals is highly dependent on the nature of the chelating ligand. A successful metal drug must both target a specific tissue or organ as well as rapidly clear from other tissues. In addition, for both imaging and tumor treatment, the target organ or tissue must have optimal exposure to the radiopharmaceutical. Therefore, there is a need for novel ligand systems designed to bind radioactive metals.

BRIEF DESCRIPTION OF THE FIGURES

FIG. 4 is a thermal ellipsoid plot of the bromide salt shown as Formula 20a;

FIG. 27*a* details as-spun fiber and FIG. 27*b* details fibers in water vapor environment for 65 hour;

SUMMARY OF THE INVENTION

Figure 1A:
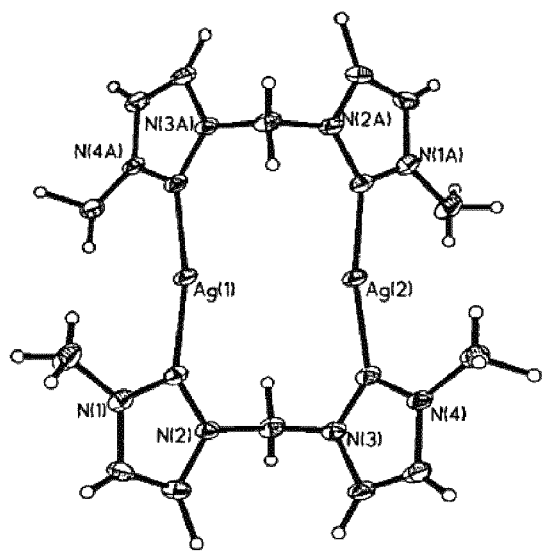
FIGS. 1*a* and 1*b* are thermal ellipsoid plots of the cationic portions of the water soluble silver dimmers shown as Formulas 9a and 9b.

The present invention generally relates to metal complexes of N-heterocyclic carbenes that contain one or more additional active moieties and/or groups therein. In one embodiment, the present invention relates to metal complexes of N-heterocyclic carbenes that contain an anti-fungal and/or anti-microbial moiety and/or group in combination with one or more additional active moieties and/or groups selected from fluoroquinolone compounds or derivatives thereof; steroids or derivatives thereof; anti-inflammatory compounds or derivatives thereof; anti-fungal compounds or derivatives thereof; anti-bacterial compounds or derivatives thereof; antagonist compounds or derivatives thereof; $H_2$ receptor compounds or derivatives thereof; chemotherapy compounds or derivatives thereof; tumor suppressor compounds or derivatives thereof; or $C_1$ to $C_{16}$ alkyl heteroatom groups where the heterotatom is selected from S, O, or N. In still another embodiment, the present invention relates to metal complexes of N-heterocyclic carbenes that contain an anti-fungal and/or anti-microbial moiety and/or group in combination with two or more additional active moieties and/or groups selected from fluoroquinolone compounds or derivatives thereof; steroids or derivatives thereof; anti-inflammatory compounds or derivatives thereof; anti-fungal compounds or derivatives thereof; anti-bacterial compounds or derivatives thereof; antagonist compounds or derivatives thereof; $H_2$ receptor compounds or derivatives thereof; chemotherapy compounds or derivatives thereof; tumor suppressor compounds or derivatives thereof; or $C_1$ to $C_{16}$ alkyl heteroatom groups where the heterotatom is selected from S, O, or N.

In one embodiment, the present invention relates to a method for using and/or administering a silver complex of an N-heterocyclic carbene are represented by a compound according to any of the Formulas shown below. In another embodiment, the present invention relates to any silver complex of an N-heterocyclic carbene represented by the Formulas shown below:

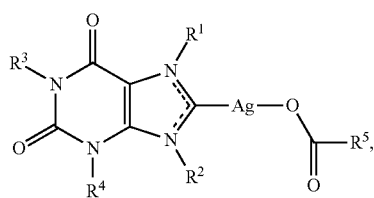

301

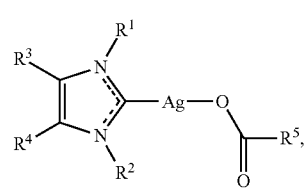

302

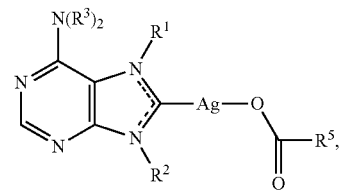

-continued

303

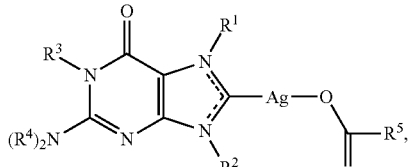

304

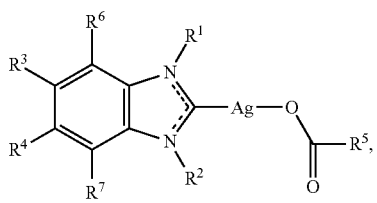

305 or suitable mixtures of two or more thereof, where $R^1$, $R^2$, $R^3$, $R^4$, $R^6$ and $R^7$, if present, are each independently selected from hydrogen; hydroxy; $C_1$ to $C_{12}$ alkyl; $C_1$ to $C_{12}$ substituted alkyl; $C_3$ to $C_{12}$ cycloalkyl; $C_3$ to $C_{12}$ substituted cycloalkyl; $C_2$ to $C_{12}$ alkenyl; $C_3$ to $C_{12}$ cycloalkenyl; $C_3$ to $C_{12}$ substituted cycloalkenyl; $C_2$ to $C_{12}$ alkynyl; $C_6$ to $C_{12}$ aryl; $C_5$ to $C_{12}$ substituted aryl; $C_6$ to $C_{12}$ arylalkyl; $C_6$ to $C_{12}$ alkylaryl; $C_3$ to $C_{12}$ heterocyclic; $C_3$ to $C_{12}$ substituted heterocyclic; $C_1$ to $C_{12}$ alkoxy; $C_1$ to $C_{12}$ alcohols; $C_1$ to $C_{12}$ carboxy; biphenyl; $C_1$ to $C_6$ alkyl biphenyl; $C_2$ to $C_6$ alkenyl biphenyl; or $C_2$ to $C_6$ alkynyl biphenyl, and where $R^5$ is selected from fluoroquinolone compounds or derivatives thereof; steroids or derivatives thereof; anti-inflammatory compounds or derivatives thereof; anti-fungal compounds or derivatives thereof; anti-bacterial compounds or derivatives thereof; antagonist compounds or derivatives thereof; $H_2$ receptor compounds or derivatives thereof; chemotherapy compounds or derivatives thereof; tumor suppressor compounds or derivatives thereof; or $C_1$ to $C_{16}$ alkyl heteroatom groups where the heterotatom is selected from S, O, or N.

DETAILED DESCRIPTION OF THE INVENTION

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention pertains.

The present invention includes a metal complex of a N-heterocyclic carbene, its method of manufacture, and methods of use. Several general types of N-heterocyclic carbene ligands may be used as ligands for a metal such as silver. These include monodentate carbenes, such as those represented by Formula 2, bidentate carbenes such as those represented by Formulas 3 through 5, and bidentate macrocyclic carbenes such as those represented by Formulas 6 and 7. With the exception of monodentate carbenes, each of these ligand types has as their basic constituent two N-heterocyclic carbene units bridged by either methylene groups, as in Formula 3, dimethylpyridine groups, as in Formula 4 and dimethylpyrrole groups as in Formula 5, or are parts of rings as in Formulas 6 and 7. The water solubility, stability, charge and lipophilicity of silver complexes of these N-heterocyclic carbenes may be modified by changes in $R_1$ and $R_2$. Each $R_1$ and $R_2$, separately or in combination, can be selected from hydrogen, $C_1$ to $C_{12}$ alkyl, $C_1$ to $C_{12}$ substituted alkyl, $C_1$ to $C_{12}$ cyclo alkyl, $C_1$ to $C_{12}$ substituted cycloalkyl, $C_1$ to $C_{12}$ alkenyl, to $C_{12}$ cycloalkenyl, $C_1$ to $C_{12}$ substituted cycloalkenyl, $C_1$ to $C_{12}$ alkynyl, $C_1$ to $C_{12}$ aryl, $C_1$ to $C_{12}$ substituted aryl, $C_1$ to $C_{12}$ arylalkyl, $C_1$ to $C_{12}$ alkylaryl, $C_1$ to $C_{12}$ heterocyclic, $C_1$ to $C_{12}$ substituted heterocyclic and $C_1$ to $C_{12}$ alkoxy. It is particularly desirable, for at least some pharmaceutical applications, for $R_1$ and $R_2$ to be selected such that the resulting metal/N-heterocyclic carbene complex is soluble and stable in an aqueous solution.

2

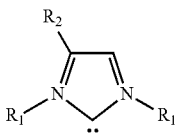

3

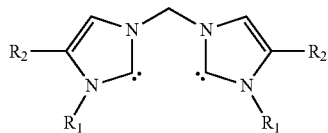

4

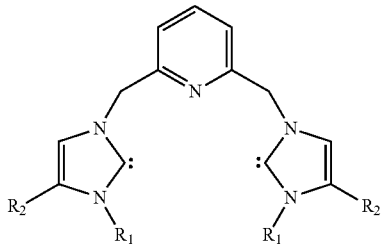

5

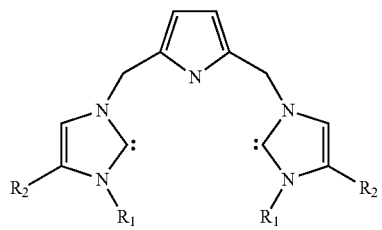

6

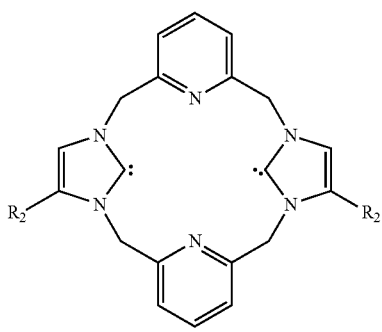

-continued

7

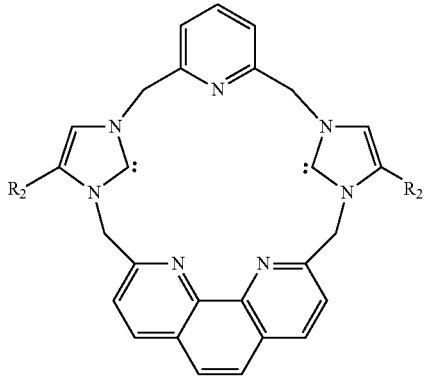

In one example, the N-heterocyclic carbene is a bidentate carbene represented by Formula 4 or 5, where $R_1$ is a $C_1$ to $C_6$ alkyl or $C_1$ to $C_6$ hydroxyalkyl group, and $R_2$ is a hydrogen atom. In one particular example, the N-heterocyclic carbene is represented by formula 4 or 5, where $R_1$ is a $C_2$ to $C_3$ hydroxyalkyl group, and $R_2$ is a hydrogen atom. In another example, the N-heterocyclic carbene is represented by Formula 4 and each adjacent $R_1$ and $R_2$ together forms a substituted alkyl group.

As stated above, in one embodiment the present invention also provides novel N-heterocyclic carbenes represented by the Formula as shown below:

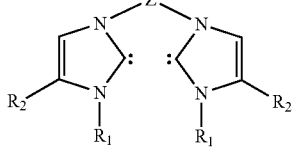

wherein Z is a heterocyclic group, and $R_1$ and $R_2$ are, independently or in combination, hydrogen or a $C_1$ to $C_{12}$ organic group selected from alkyl, substituted alkyl, cyclo alkyl, substituted cycloalkyl, alkenyl, cycloalkenyl, substituted cycloalkenyl, alkynyl, aryl, substituted aryl, arylalkyl, alkylaryl, heterocyclic, substituted heterocyclic and alkoxy groups. In one example, Z is a pyridine or a pyrrole. In another example, Z is dimethylpyridine or dimethylpyrrole.

In general, imidazolium salts are the immediate precursors of N-heterocyclic carbenes. Several procedures may be used to convert imidazolium salts to the corresponding N-heterocyclic carbenes. N-Heterocyclic carbenes may be generated from imidazolium salts by deprotonation with bases such as KOtBu, KH, and NaH in solvents such as THF and liquid ammonia. Isolatable N-heterocyclic carbenes may replace two-electron donors (such as tetrahydrofuran, carbon monoxide, nitriles, phosphines, and pyridine) on a variety of transition metal complexes to give N-heterocyclic carbene transition metal complexes. However it has not always been practical to isolate the carbenes.

N-Heterocyclic carbene complexes may also be obtained by in situ generation of the N-heterocyclic carbene by deprotonation of the corresponding imidazolium salts in the presence of a suitable transition metal complex. Basic ligands on the metal complex, such as hydride, alkoxide, or acetate can deprotonate the imidazolium salt to form the N-heterocyclic carbene that readily binds to the vacant coordination site on a metal. For example Pd(OAc)$_2$ has been shown to react with a variety of imidazolium salts to form palladium-carbene complexes.

The imidazolium salt can also be treated with an inorganic or organic base to generate the carbene. The reaction of imidazolium salts with metals containing basic substituents has been shown to be quite useful for the synthesis of transition metal complexes of carbenes. The combination of the basic oxide, Ag$_2$O, with imidazolium salts may be used to generate silver-carbene complexes. The use of silver-carbene complexes as carbene transfer reagents has been used to provide carbene complexes of gold(I) and palladium(II). Silver-carbene complexes have been employed in this manner to provide complexes with Pd-carbene and Cu-carbene bonds. The formation of transition metal-carbene bonds, using carbene transfer reagents is favored in many situations because the reactions proceed under mild conditions and without the use of strong bases. For example, the condensation of 2 equivalents of n-butyl imidazole or methyl imidazole and 1 equivalent of diiodomethane in refluxing THF affords the imidazolium salts shown as Formulas 8a or 8b in high yield. The combination of shown as Formulas 8a or 8b with Ag$_2$O in water forms the water soluble silver dimers 9a and 9b, respectively.

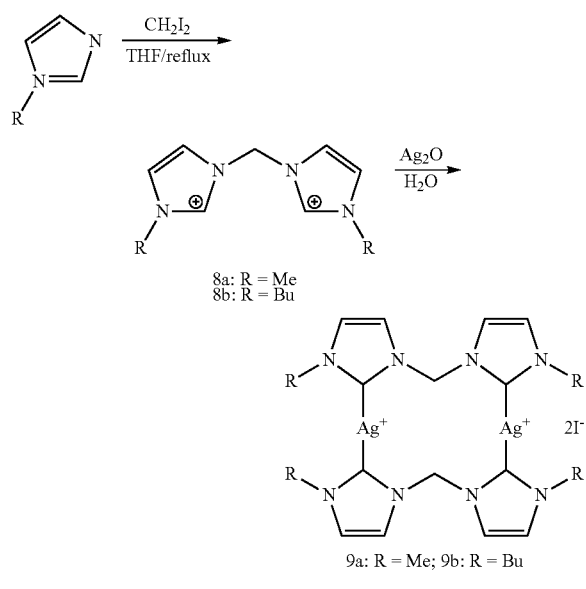

The combination of two equivalents of 1-iodoethanol (Formula 12) with bisimidazol (Formula 11) in refluxing butanol gives the water soluble diol shown as Formula 13. This compound has been characterized by both NMR and X-ray crystallography.

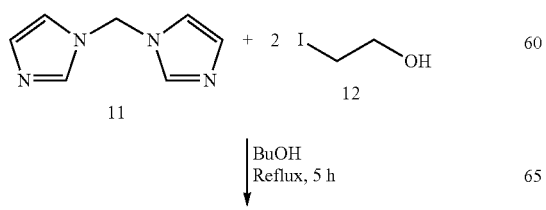

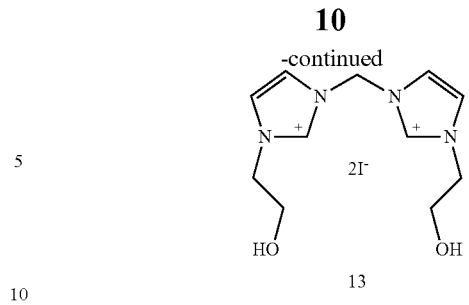

A similar reaction has been carried out using 1,2-dibromoethane (formula 14) with bisimidazol to form the carbene represented by Formula 15. The alcohol groups of Formula 13 and the bromides of Formula 15 provide functionalized sites for the incorporation of solubilizing moieties.

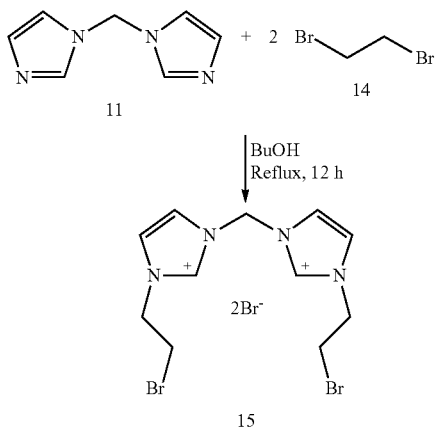

The pincer ligands 2,6-bis-(n-butylimidazoliummethyl) pyridine dihalide (Formulas 16a and 16b) are easily obtained by the reaction of N-butyl imidazole with 2,6-bis(halogenmethyl)pyridine in a 2:1 molar ratio respectively. Ligand 16a readily reacts with Ag$_2$O in CH$_2$Cl$_2$ to yield the silver carbene complex 17. Complex 17 is stable in air and light.

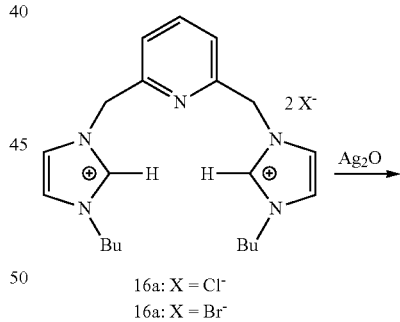

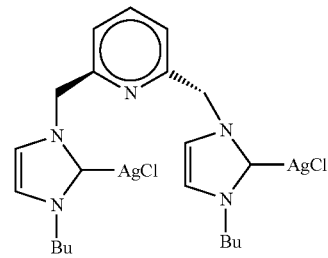

A general synthesis of pincer N-heterocyclic carbenes with a pyridine as the bridging unit is presented below. The reaction of two equivalents of potassium imidazole with 2,6-bis (bromomethyl)pyridine resulted in Formula 19 in 70% yield. The combination of the compound represented by Formula 18 with 2-bromoethanol or 3-bromopropanol gives Formulas 19a and 19b, respectively. The combination of the Br salt of Formulas 19a or 19b with an equimolar amount of Ag$_2$O gives the silver biscarbene polymers 20a and 20b, respectively. Formula 20a has been crystallographically characterized. The bromide salts represented by Formulas 20a and 20b are very soluble and slowly decompose in water to give a silver mirror on the side of a flask containing either compound. Formula 20a and its propanol analog Formula 20b are effective antimicrobials. Derivatives of these complexes can be synthesized, using histidine as an example precursor as outlined below, to improve their antimicrobial properties.

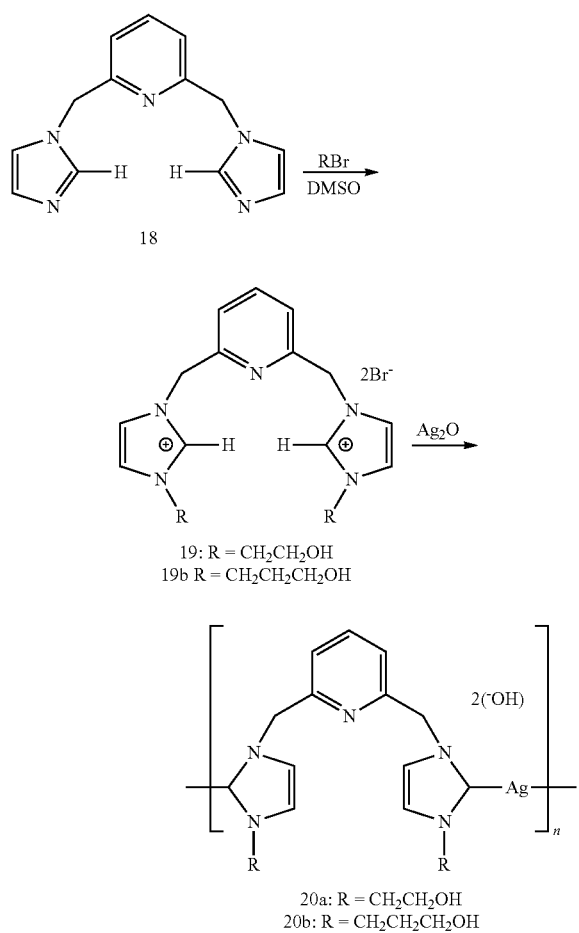

The antimicrobial activity of water soluble silver (I) N-heterocyclic carbene 20a, in reference to silver nitrate, was investigated on yeast and fungi (*Candida albicans, Aspergillus niger*, Mucorales, *Saccharomyces cerevisiae*) using the LB broth dilutions technique, and bacteria (*E. coli, S. aureus, P. aeruginosa*) of clinical importance. The sensitivity test of the silver compounds using the Kirby-Bauer agar diffusion (filter paper disk) procedure, shows that silver (I) N-heterocyclic carbenes exhibit antimicrobial activity as effective as silver nitrate on all the bacteria by measuring the zone of growth inhibition using filter paper disks impregnated with solutions of the silver compound placed on a lawn of organism on an agar plate. Overnight cultures containing various concentrations of the silver compounds and bacteria or fungi were examined for growth. For each organism, the tube containing the minimum inhibitory concentration (MIC) for each silver compound was used to inoculate agar plates to confirm the absence of viable organisms in that culture. Formula 20a was effective on bacteria and fungi at lower concentrations, and had a longer period of silver activity than silver nitrate over the 7 day time course of the experiment. Toxicity studies with rats have shown that ligand 19a, the precursor to 20a and the material that forms on degradation of 20a, is of low toxicity and clears within two days through the kidneys as determined by mass spectroscopy of the urine.

Figure 5:
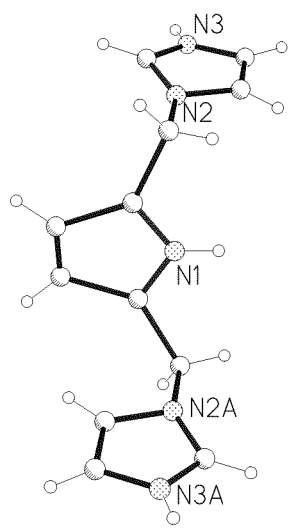
FIG. 5 is a thermal ellipsoid plot of the compound shown as Formula 23.

The combination of two equivalents of potassium imidazole (Formula 21) with 2,5-bis(trimethylaminomethyl)pyrrole diiodide (Formula 22) in THF gives Formula 23. Formula 23 has been crystallographically characterized and its thermal ellipsoid plot is shown as FIG. 5. Addition of two equivalents of butyl bromide to Formula 23 gives Formula 24 in high yield.

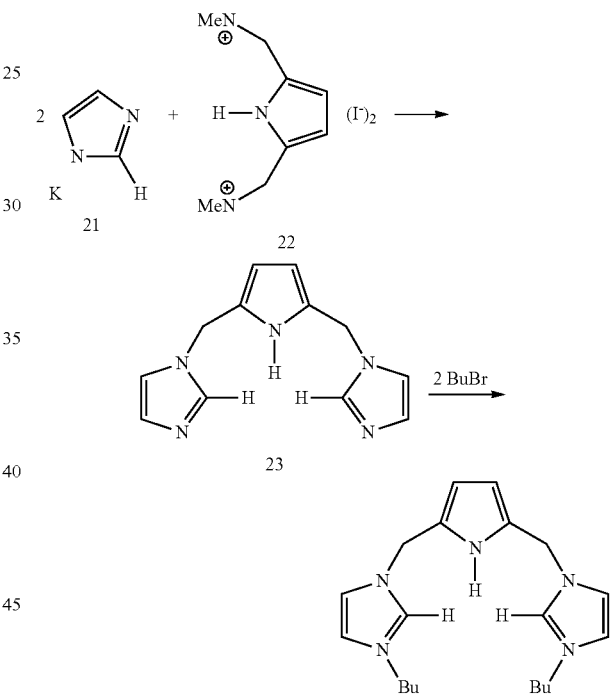

Figure 6:
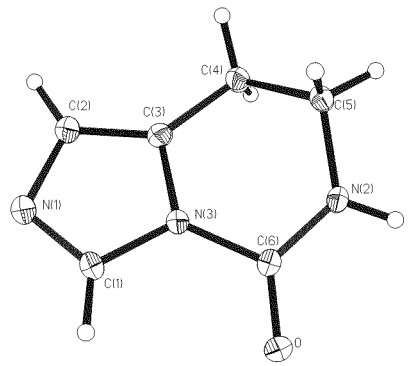
FIG. 6 is a thermal ellipsoid plot of 5,6,7,8-tetrahydro-5-oxoimidazo [1,5-c]pyrimidine shown as Formula 26.
Figure 7:
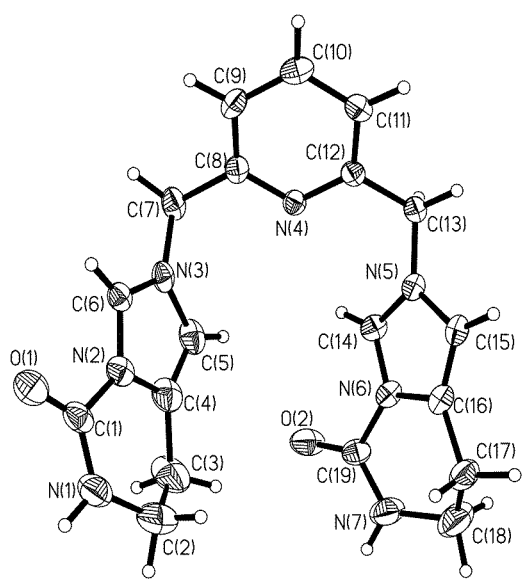
FIG. 7 is a thermal ellipsoid plot of the compound shown as Formula 27.
Figure 8:
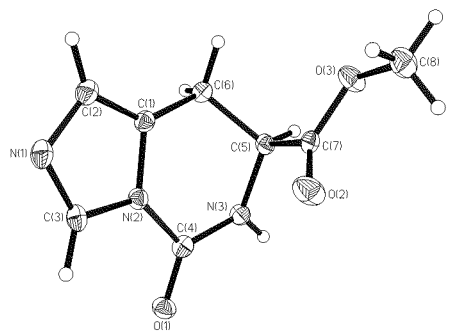
FIG. 8 is a thermal ellipsoid plot of the compound shown as Formula 29b.
Figure 9:
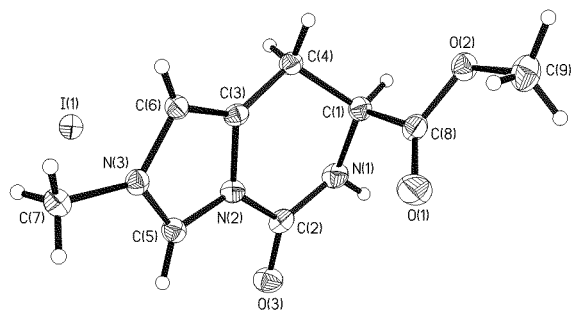
FIG. 9 is a thermal ellipsoid plot of the compound of the iodide salt shown as Formula 30b.

The reaction of histamine dihydrochloride (Formula 25) with carbonyldiimidazole in DMF resulted in 5,6,7,8-tetrahydro-5-oxoimidazo[1,5-c]pyrimidine (Formula 26) in 40% yield. The compound of Formula 26 has been crystallographically characterized (see thermal ellipsoid plot in FIG. 6). The combination of two equivalents of Formula 26 with one equivalent of 2,6-bis(bromomethyl)pyridine in acetonitrile resulted in the formation of Formula 27 in very high yield.

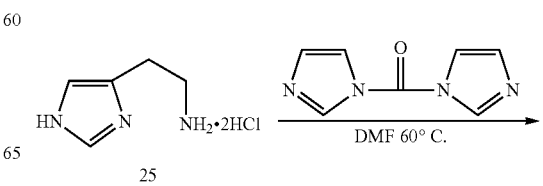

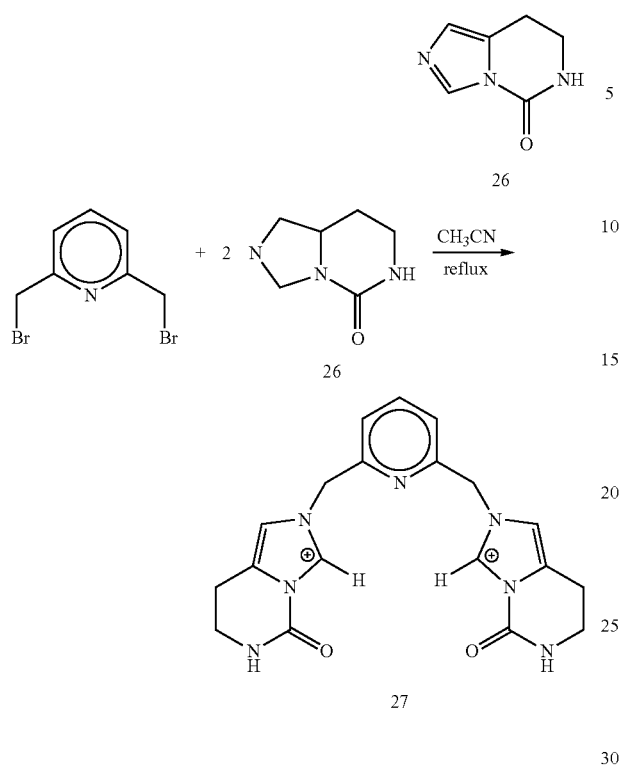

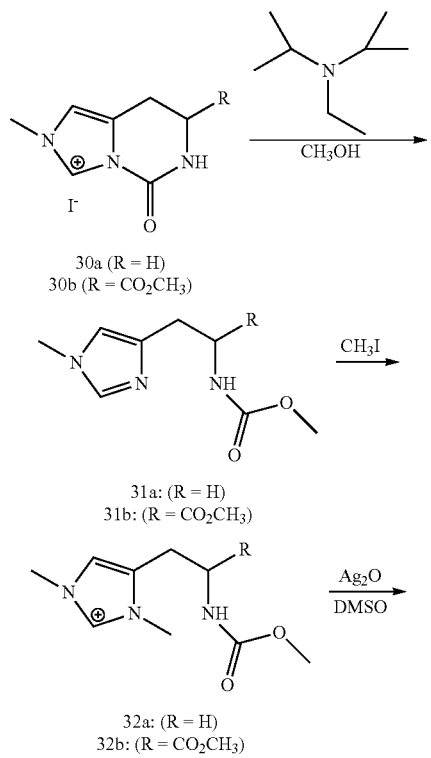

Methylated histamine and histidine are also expected to have low toxicity because histamine and histidine occur naturally in the body. The reaction of L-histidine methyl ester dihydrochloride Formula 28 with carbonyldiimidazole in DMF results in Formula 29. The combination of three equivalents of iodomethane with Formula 29 in refluxing acetonitrile gives Formula 30. The iodide salt of Formula 30 is reacted with methanol in the presence of N,N-diisopropylethylamine at reflux for 3 days to obtain 1-methyl-L-histidine Formula 31. The combination of three equivalents of iodomethane with Formula 31 in refluxing acetonitrile gives 1,3-dimethyl-L-histidine Formula 32. The combination of Formula 32 with $Ag_2O$ in DMSO forms the silver carbene Complex 33. Formula 33b has been shown to have significant antimicrobial activity against *Staphylococcus aureus*, *Escherichia coli* and *Pseudomonas aeruginosa* by the Kirby-Bauer technique.

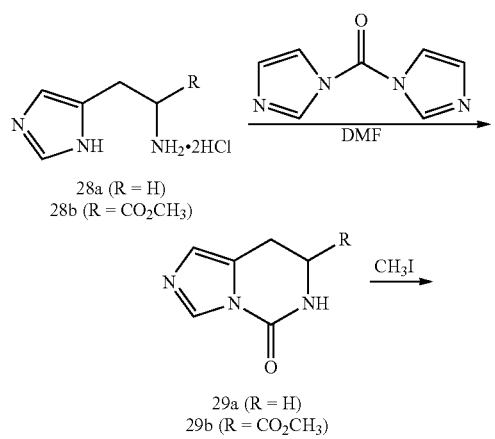

Figure 10:
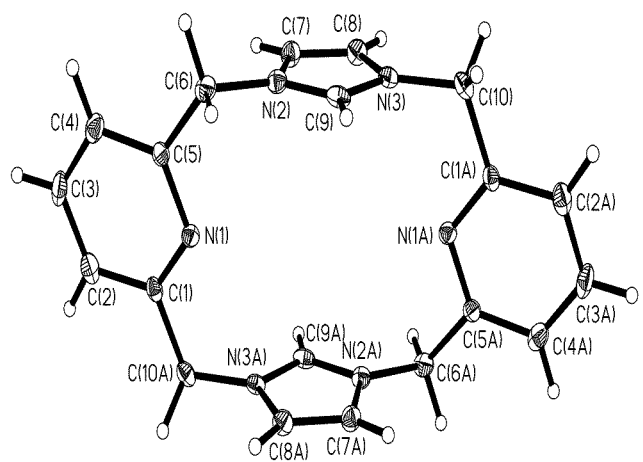
FIG. 10 is a thermal ellipsoid plot of [$PF_6^-$] salt of Formula 36.
Figure 11:
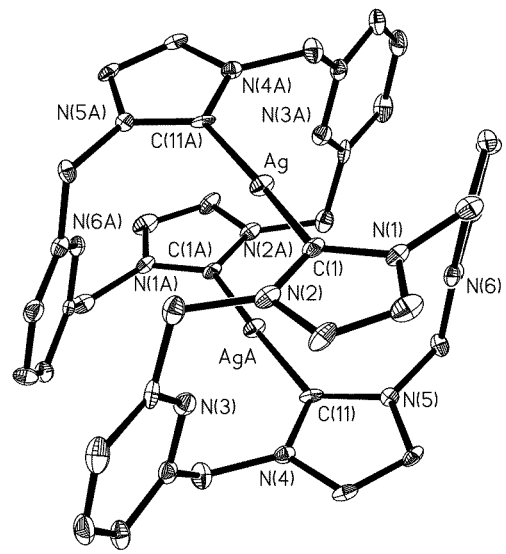
FIG. 11 is a thermal ellipsoid plot of the silver biscarbene dimmer shown as Formula 37.
Figure 12:
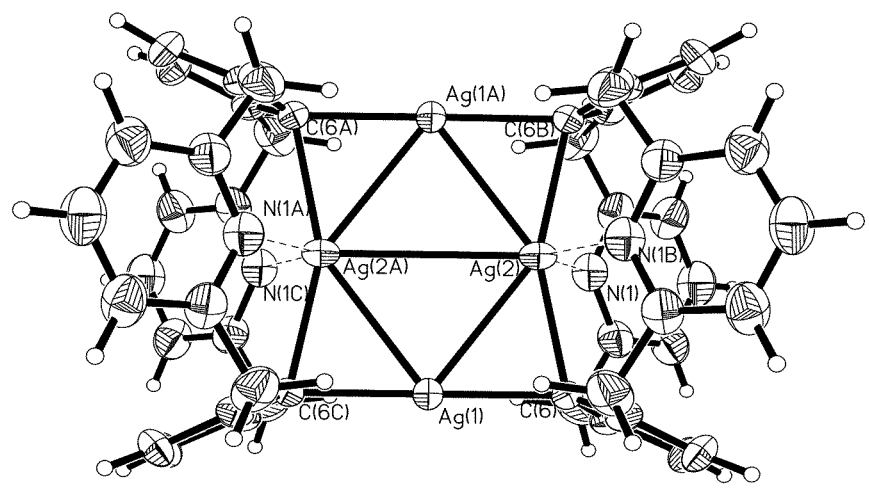
FIG. 12 is a thermal ellipsoid plot of the tetracationic portion of Formula 38 [$PF_6$]$_4$.
Figure 13:
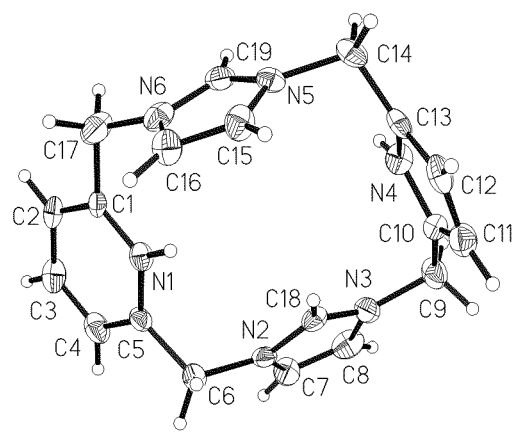
FIG. 13 is a thermal ellipsoid plot of the compound shown as Formula 39b.

Macrocyclic N-heterocyclic carbenes may be synthesized according to the following method. The reaction of two equivalents of potassium imidazole with 2,6-bis(bromomethyl)pyridine (Formula 34) resulted in the compound of Formula 35 in 70% yield. The combination of Formula 35 with the compound of Formula 34 in DMSO gave the compound of Formula 36 in 80% yield. The combination of the $PF_6^-$ salt of Formula 36 with an equimolar amount of $Ag_2O$ gives a silver biscarbene dimer (Formula 37) in nearly quantitative yield. Formulas 36 and 37 have been crystallographically characterized and are represented in FIG. 10 and FIG. 11, respectively. The bromide salt of Formula 37 (X=Br), is soluble and stable in water. Under analogous reaction conditions, the combination of Formula 36 with 4 equivalents of $Ag_2O$ gives a tetra-silver biscarbene dimer (not shown, but ref. to as Formula 38 and FIG. 12). The combination of Formula 36 ($X^-=Br^-$) with $Ag_2O$ in water directly gives the bromide salt of Formula 37. Halide salts of Formula 37 can be synthesized in water, and are water soluble. The bromide and chloride salts of Formula 37 are effective antimicrobials.

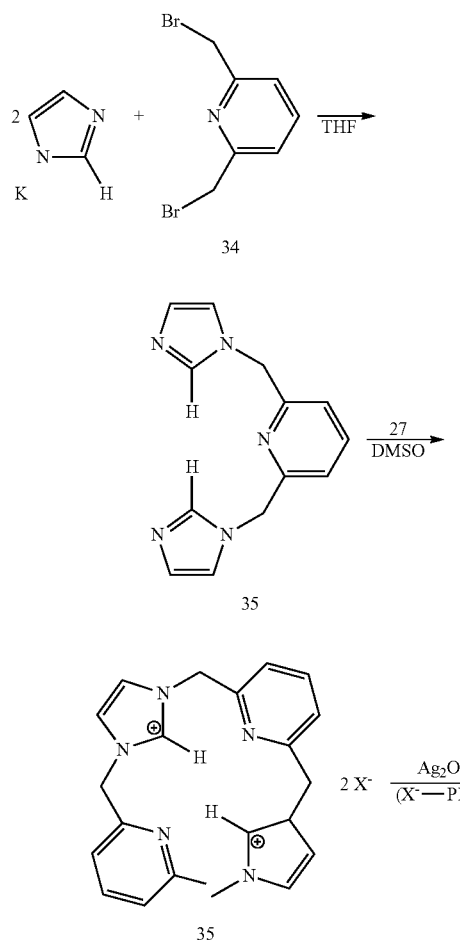

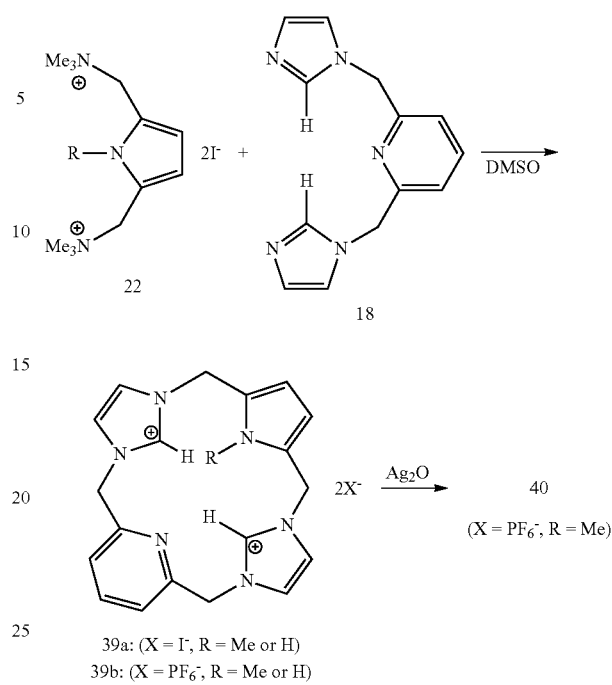

39a: (X = I⁻, R = Me or H)
39b: (X = PF₆⁻, R = Me or H)

Figure 15:
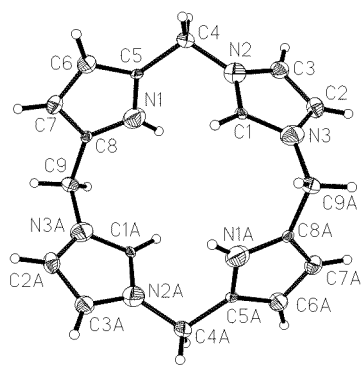
FIG. 15 is a thermal ellipsoid plot of the compound shown as Formula 41.
Figure 16:
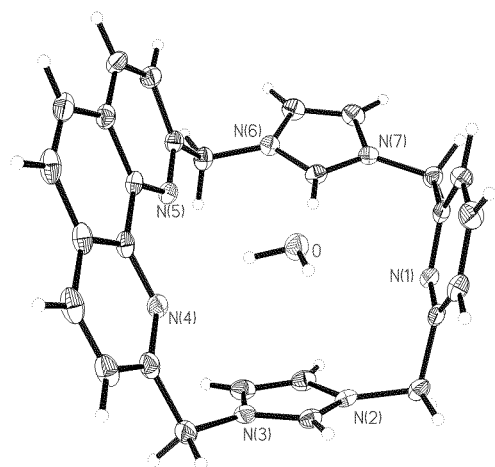
FIG. 16 is a thermal ellipsoid plot of the dibromide salt show as Formula 43.
Figure 17:
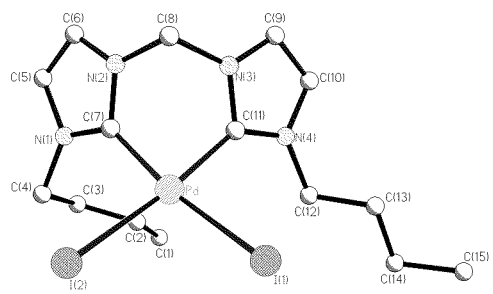
FIG. 17 is a thermal ellipsoid plot of the compound shown as Formula 8c.
Figure 18:
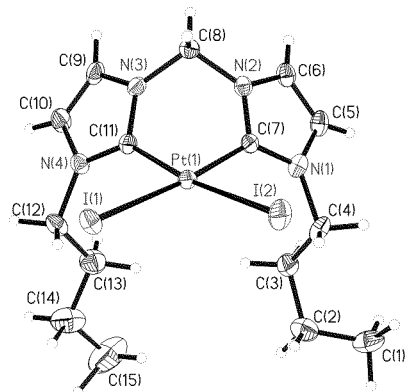
FIG. 18 is a thermal ellipsoid plot of the compound shown as Formula 8d.
Figure 19:
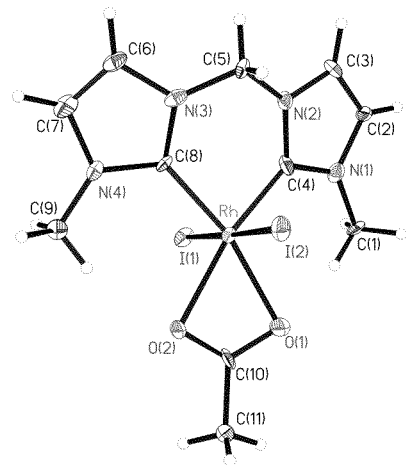
FIG. 19 is a thermal ellipsoid plot of the rhodium carbene shown as Formula 8e.
Figure 20:
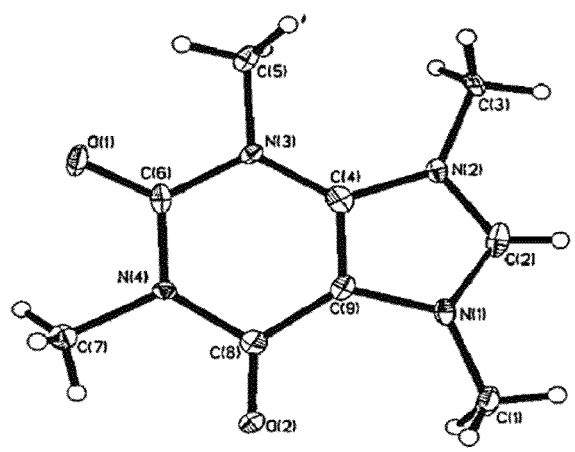
FIG. 20 is a thermal ellipsoid plot of the compound shown as Formula 96b.
Figure 21:
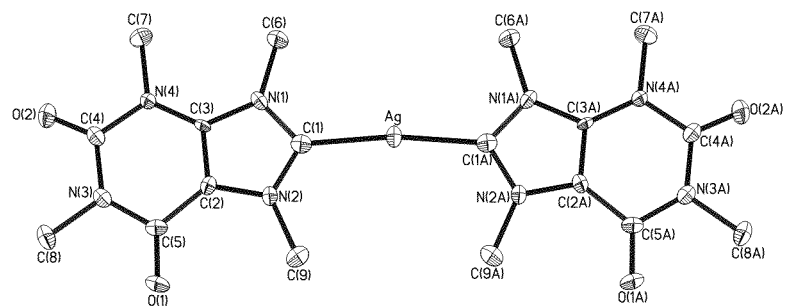
FIG. 21 is a thermal ellipsoid plot of the compound shown as Formula 97b.
Figure 22:
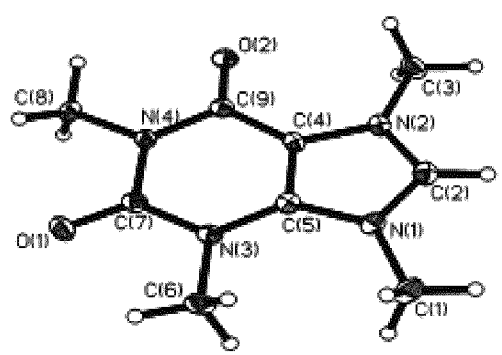
FIG. 22 is a thermal ellipsoid plot of the compound shown as Formula 98.
Figure 23:
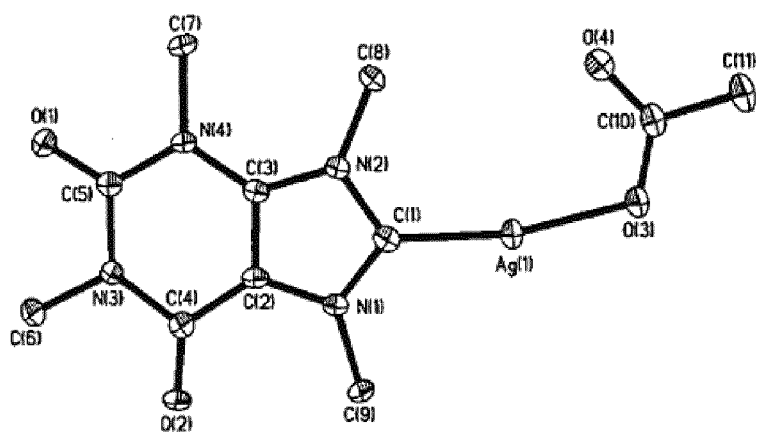
FIG. 23 is a thermal ellipsoid plot of the compound shown as Formula 100.

Addition of one equivalent of Formula 22 to Formula 23 gives the bisimidazolium porphyrinoid of Formula 41 in high yield and on a large scale. Formula 41 has been crystallographically characterized and the thermal ellipsoid plot of the dication ring of Formula 41 is shown as FIG. 15. The combination of Formulas 39 (R=H) and 41 with 4 equivalents of Ag₂O affords tetra-silver biscarbene dimers analogous to Formulas 38 and 40.

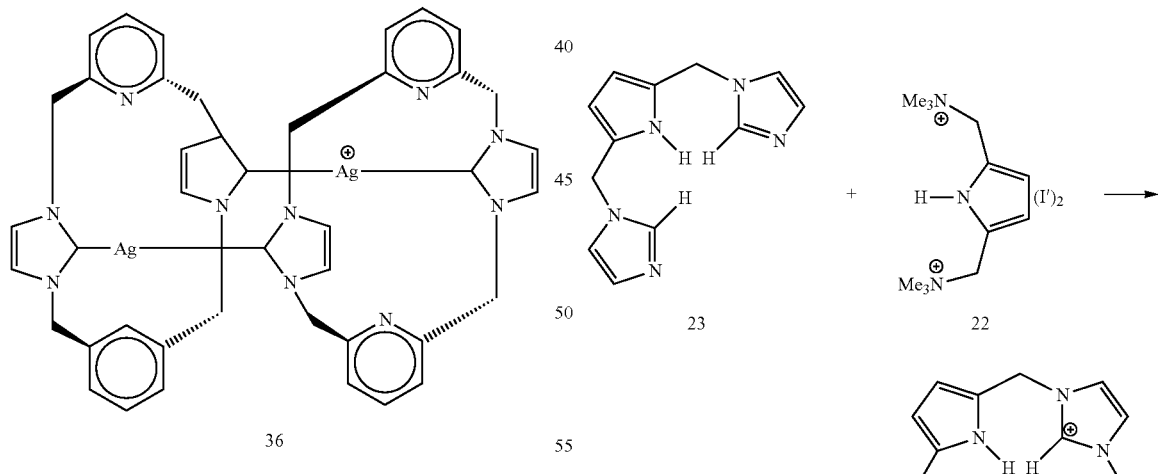

Figure 14:
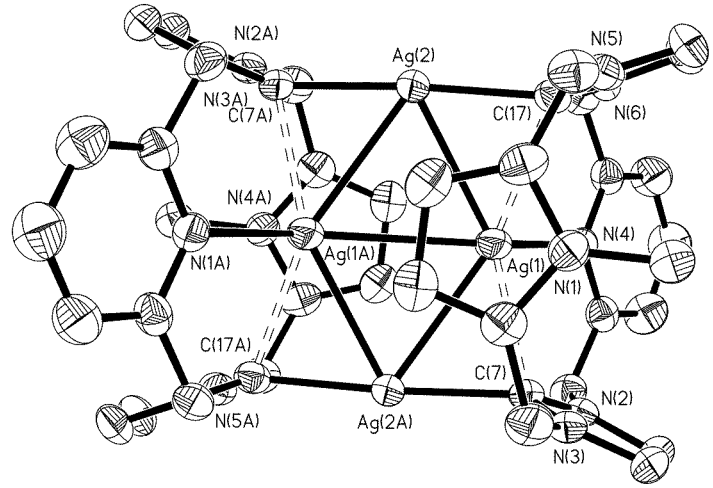
FIG. 14 is a thermal ellipsoid plot of the tetracationic portion of Formula 40 [$PF_6$]$_4$.

The 3+1 condensation of the pyrrole shown by Formula 22 (R=H or Me), with the pyridine shown by Formula 18 gives the compound of Formula 39 (R=H or Me). Anion exchange of Formula 39a with NH₄⁺PF₆⁻ gives Formula 39b. The combination of Formula 39b (X=PF₆⁻, R=Me) with four equivalents of Ag₂O gives a tetra-silver biscarbene dimer, Formula 40 (X=PF₆⁻, R=Me), the thermal ellipsoid plot of which is shown in FIG. 14.

The combination of Formula 18 with the bis(bromomethyl)phenanthroline of Formula 42 affords the expanded macrocycle of Formula 43 as a dibromide salt.

17

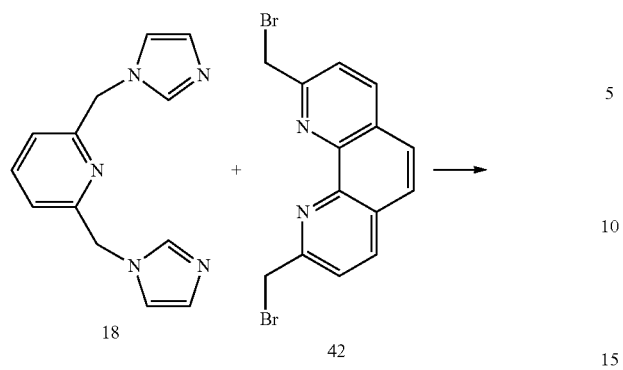

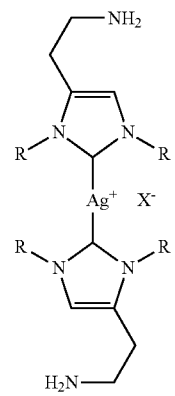

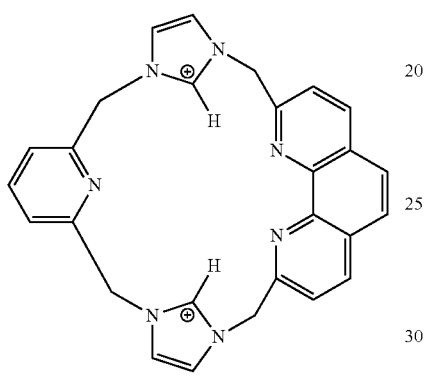

18
-continued

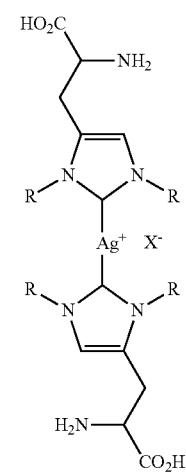

Monodentate N-heterocyclic carbene silver complexes such as those represented by Formula 48 may be synthesized by the interaction of the imidazolium precursors of Formula 44 with silver oxide. As mentioned above, the side chains, R, may be chosen so as to modify the water solubility, lipophilicity and other properties of the complexes. For example, R may be hydrogen or a $C_1$ to $C_{12}$ organic group selected from alkyl, cycloalkyl, alkenyl, cycloalkenyl, alkynyl, aryl, arylalkyl, alkylaryl, heterocyclic, and alkoxy groups and substituted derivatives thereof. Silver complexes such as those represented by Formulas 46 and 47, synthesized from histamine and histidine, respectively, can be synthesized and used as antimicrobial compounds. Because histamine and histidine are present in the body, their derivatives are expected to give the least skin irritation when used as a topical antimicrobial and to provide very limited problems as an internal antimicrobial with excellent toxicological properties.

The synthesis of the pincer N-heterocyclic carbenes having methene or methylene groups bridging the two N-heterocyclic carbenes (see Formula 3) and with substituents attached is provided below. The substituents may be chosen in order to give the overall complex sufficient solubility, lipophilicity or other properties. Pyridine rings and imidazoles serve as the fundamental building blocks in the procedures discussed below. Based on the synthesis of Formulas 8a and 8b above, two equivalents of Formula 58 will combine with methylene iodide to form the compound of Formula 59. Opening of Formula 59 with HCl will provide the compound of Formula 60. One equivalent of an alkyl halide would readily add to the primary amines of Formula 60, because primary amines are more reactive than imidazole nitrogens, to form Formula 61. A second alkyl halide would add to the secondary imidazole nitrogens of Formula 61 to form the bisimidazolium cation shown as in Formula 62. The bisimidazolium cation 62 may be combined with $Ag_2O$ to form silver complexes shown as Formula 63 similar to Formulas 9a and 9b above.

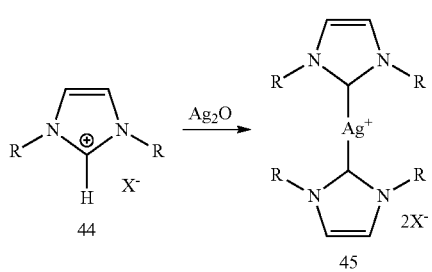

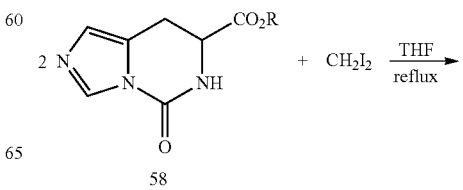

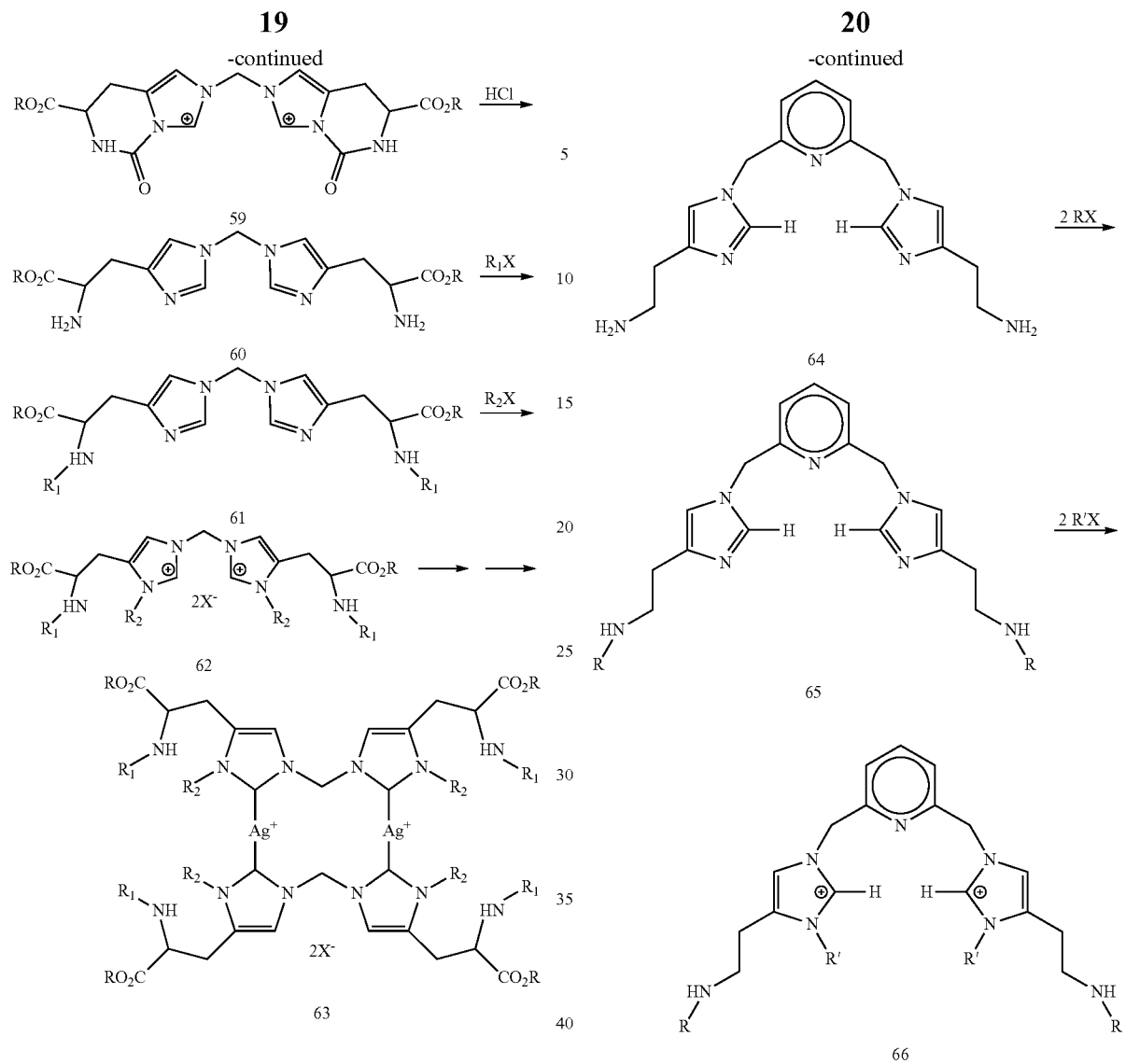

Formula 27 can be treated with HCl to give Formula 64, which can then be contacted with a derivatized alkyl halide containing a solubilizing substituent to give Formula 65. Formula 64 could also be derivatized with a carboxylic acid and dicyclohexylcarbodiimide (DCC) to form an amide bond. The combination of Formula 65 at a higher temperature with a derivatized alkyl halide that similarly contains a solubilizing substituent will give the imidazolium biscation shown as Formula 66, which can be further complexed with metals such as rhodium.

Silver-carbene complexes may also be used as carbene transfer reagents to create other carbene complexes. The formation of transition metal-carbene bonds, using carbene transfer reagents is favored in many situations because the reactions proceed under mild conditions and without the use of strong bases. For example, the combination of Formula 8b with Pd(OAc)$_2$ in DMF followed by treatment with NaI in acetonitrile results in the formation of the compound represented by Formula 8c. The thermal ellipsoid plot of this compound is shown below. Similarly, the combination of Formula 8b with PtCl$_2$ and sodium acetate in DMSO gives the compound represented by Formula 8d in 50% yield.

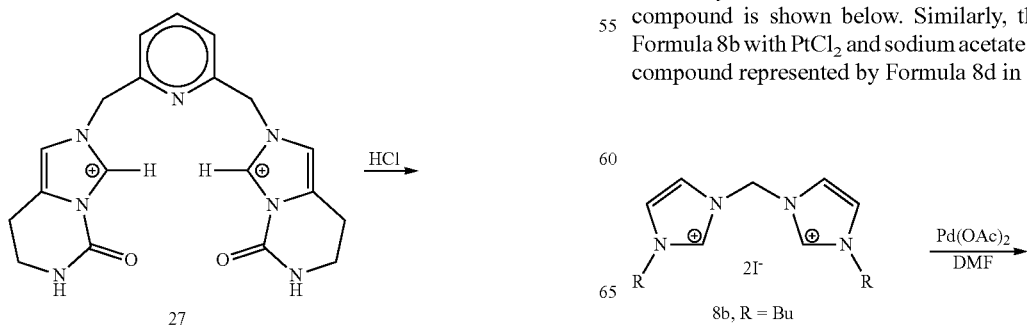

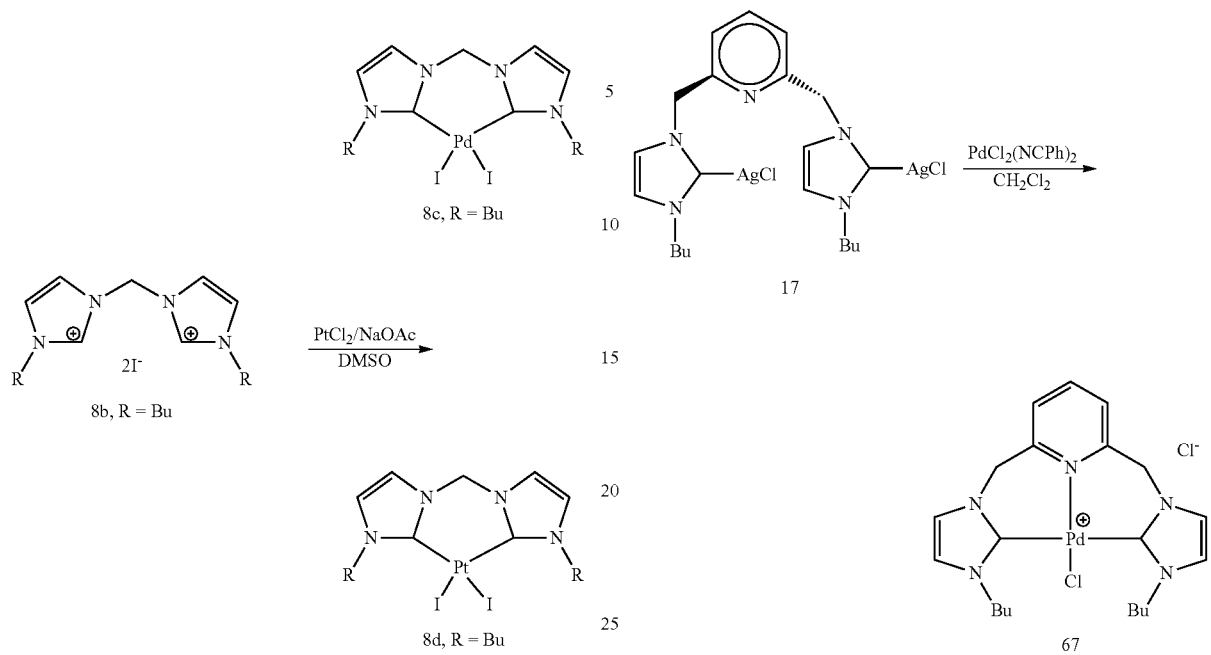

The combination of the imidazolium salt represented by Formula 8a with [(1,5-cyclooctadiene)RhCl]$_2$ in refluxing MeCN in the presence of NaOAc and KI gives the rhodium carbene of Formula 8e in 80% yield. This compound has been characterized by $^1$H and $^{13}$C NMR and X-ray crystallography. This rhodium complex is water stable for extended periods of time. A related chelating bis-carbene rhodium complex has been synthesized and has been shown to be stable enough to use in catalytic processes.

The silver complex of an N-heterocyclic carbene represented by Formula 17 can function as a carbene transfer reagent. The reaction of Formula 17 with (PhCN)$_2$PdCl$_2$ in CH$_2$Cl$_2$ yields the palladium carbene complex represented by Formula 67 and two equivalents of AgCl in nearly quantitative yield.

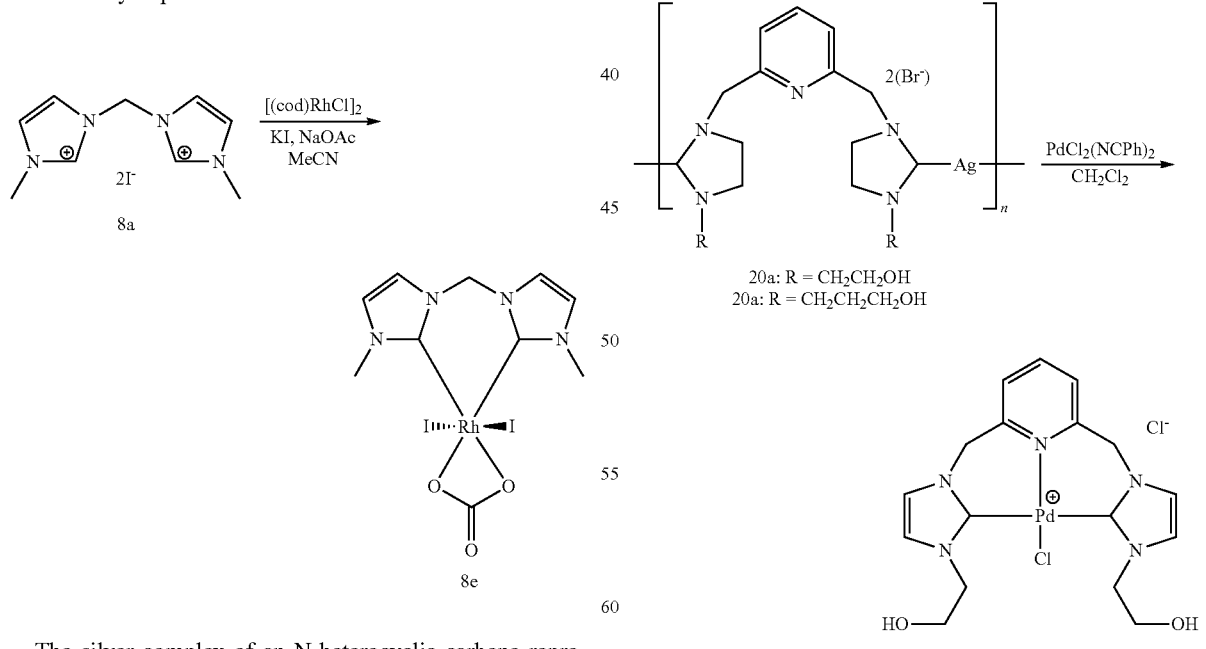

Similarly, the reaction of the complex represented by Formula 20a with (PhCN)$_2$PdCl$_2$ in CH$_2$Cl$_2$ yields the palladium carbene complex represented by Formula 68.

A similar synthesis route may be used to synthesize the compound represented by Formula 69 from the compound represented by Formula 19a.

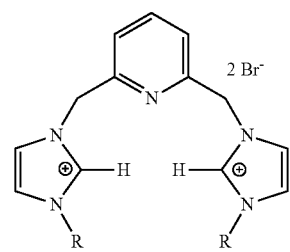

19a: R = CH₂CH₂OH
19a: R = CH₂CH₂CH₂OH

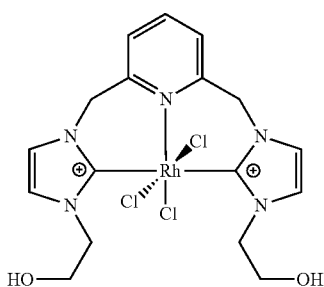

For the synthesis of pyrrole bridged pincer N-heterocyclic carbenes, a 2,5-bisdimethylpyrrole with leaving groups on the methyl groups is particularly useful in the synthesis method of the present invention. The Mannich reaction of dimethylammonium chloride in aqueous formaldehyde and pyrrole gives 2,5-bisdimethylaminomethylpyrrole, represented by Formula 70. Addition of iodomethane to the pyrrole represented by Formula 70 in THF gives 2,5-bis(trimethylaminomethyl)pyrrole diiodide (Formula 71).

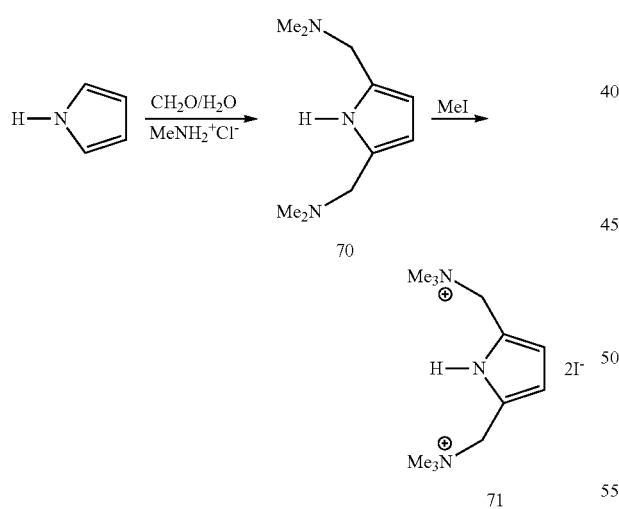

A molecule containing a 2-nitroimidazole group is believed to be targeted to hypoxic cells. These compounds are reduced at the nitroimidazole group and trapped within cells with a low oxygen environment. Attachment of a 2-nitroimidazole group to pincer N-heterocyclic carbenes to form the compound represented by Formula 73 may be accomplished as follows. The condensation of the compound represented by Formula 72 with bisimidazol in a 2:1 ratio is expected to give the compound represented by Formula 73. Other derivatives of 2-nitroimidazole having various linker segments may similarly be synthesized. The variety of linker groups, including polyethylene oxide (PEO), will allow for flexibility in positioning the chelator relative to the targeting group as well as for variation of the octanol/water partition coefficient of the compound, which is relevant to the clearance through the kidneys. The formation of rhodium complexes similar to Formula 73 is also envisioned. Similar procedures may be used to synthesize derivatives represented by Formulas 75 and 76 containing nitroimidazole and solubilizing substituents.

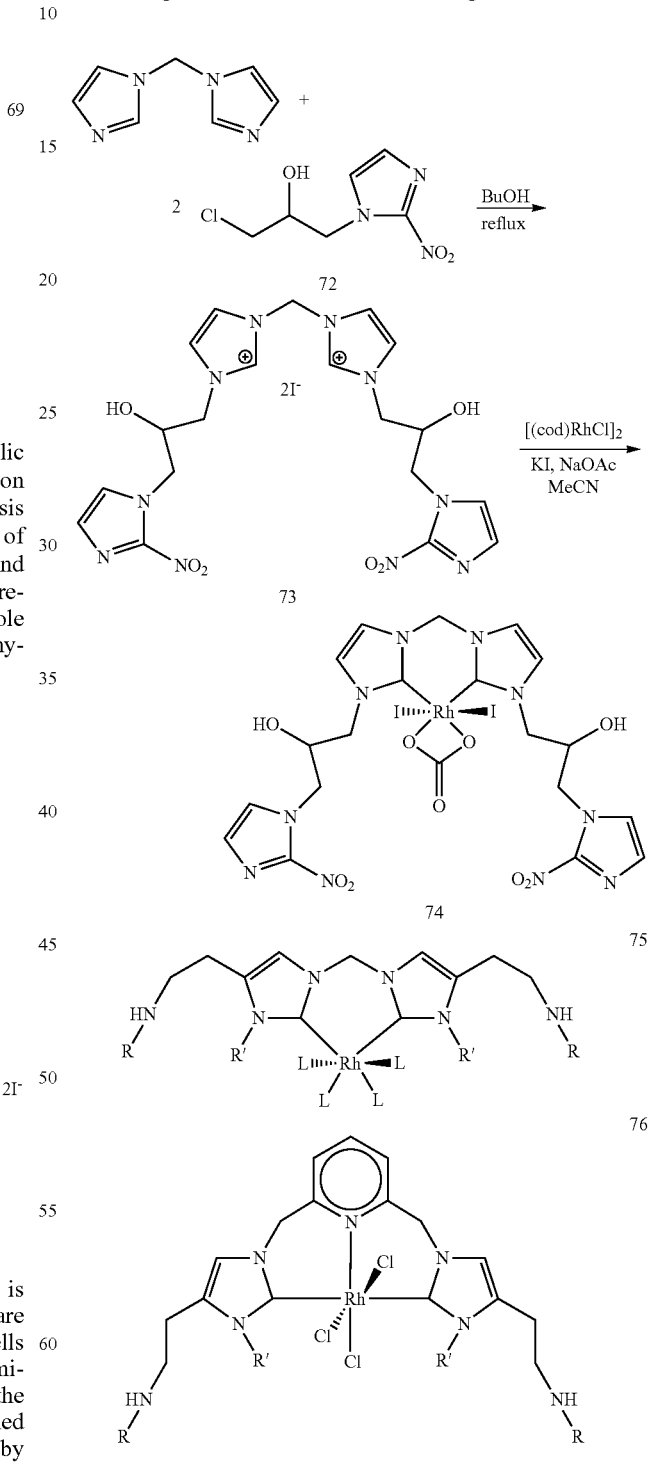

Isotopes of the metals indicated herein as components of an N-heterocyclic carbene complex may be used to form radiopharmaceuticals. For example, $^{105}$Rh may be used in place of Rh. $^{105}$Rh has a convenient half-life of 1.5 days and also emits relatively low levels of γ-radiation. This isotope of rhodium decomposes by beta emission to $^{105}$Pd a stable naturally occurring isotope of palladium. Other employable isotopes can be selected from transition metals, elements from the lanthanide series, and elements from the actinide series. Preferred isotopes are Ag, Rh, Ga, and Tc.

As mentioned above, the present invention includes metal N-heterocyclic carbene complexes that can be made from several N-heterocyclic carbene precursors, the imidazolium salts. The imidazolium salts obtained from biological analogs, such as the purine bases which includes xanthine, hypoxanthine, adenine, guanine and there derivatives can readily be reacted with silver(I) oxide in suitable solvent to obtain the silver-N-heterocyclic carbene complexes. The imidazolium cations can easily be classified as mono-imidazolium cation such as those represented by Formulas 77 through 81, bis-imidazolium cations such as those represented by one of the following Formulas:

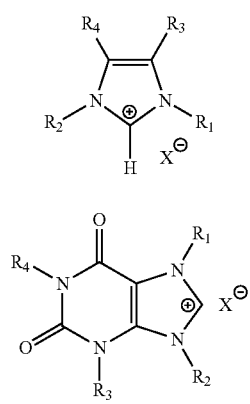

77

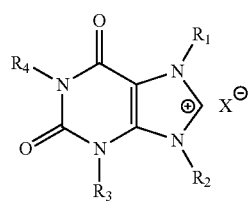

78

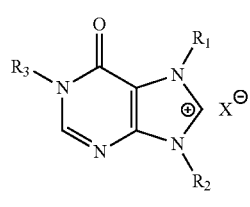

79

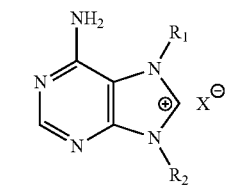

80

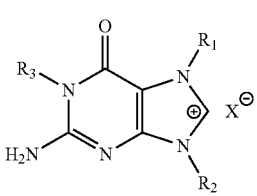

81

Preferable mono-imidazolium cations include those represented by Formulas 48 through 52:

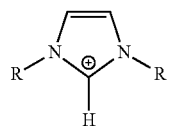

48

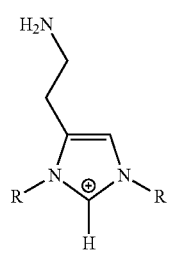

49

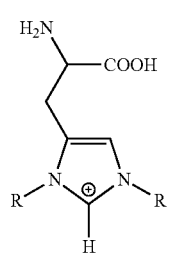

50

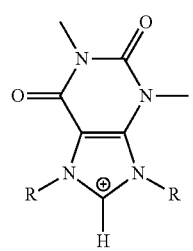

51

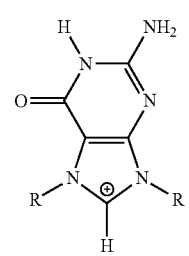

52 which can be used for the formation of preferred monodentate N-heterocyclic carbene silver complexes, such as those having Formulas 53 through 57, respectively. The carbene silver complexes shown in Formulas 53 through 57 can be synthesized by the interaction of the imidazolium precursors 48 through 52, respectively, with a silver oxide:

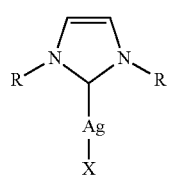

53

54
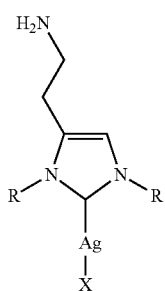
55
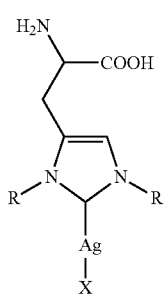
56
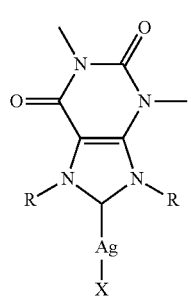
57
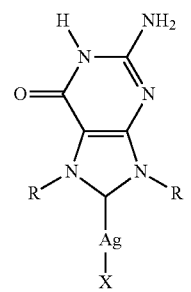
Similarly, multi-imidazolium cations according to the present invention include those represented by Formulas 82 through 90:
82
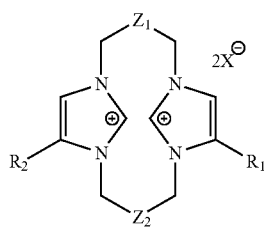
83
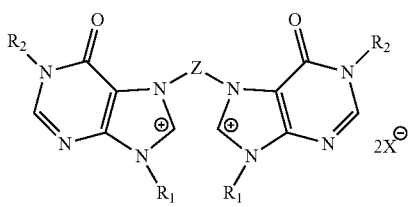
84
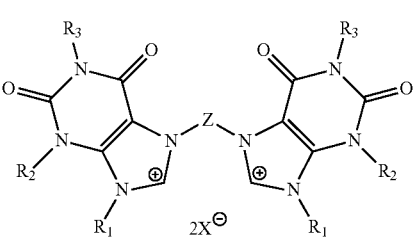
85
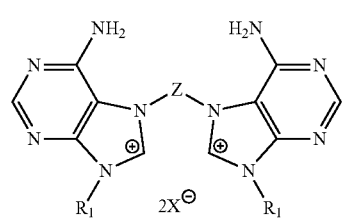
86
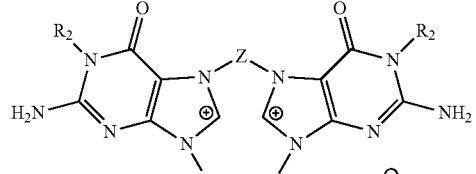
87
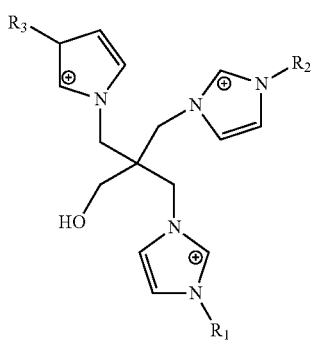
88
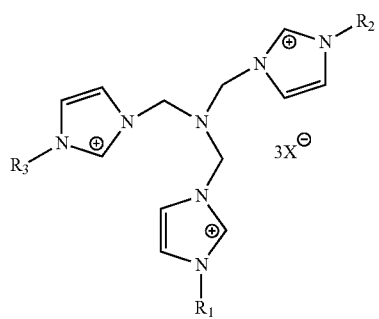

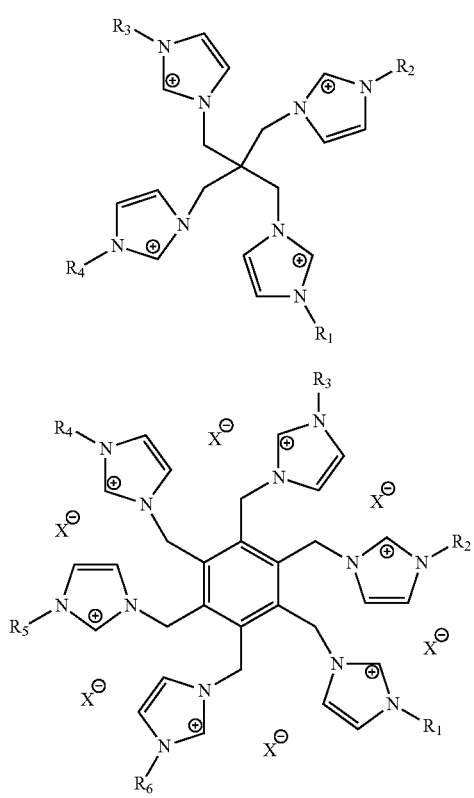

89

90

The bis-imidazolium cations bridged can be represented by Z, wherein Z can be a methylene, heterocyclic group, dimethyl heterocyclic group, dimethyl cycloalkane group, dimethyl substituted heterocyclic group, aryl group, dimethyl substituted aryl group. The bis-imidazolium cations can be bridge by $Z_1$ and $Z_2$ to form a ring (cyclophane), wherein $Z_1$ and $Z_2$ can each be separate or in combination, and can be selected from heterocyclic, $C_1$ to $C_{12}$ substituted heterocyclic, aryl, $C_1$ to $C_{12}$ substituted aryl, $C_3$ to $C_{12}$ substituted ketone, and $C_1$ to $C_{12}$ alkylene groups. Each R group; $R_1$, $R_2$, $R_3$ and $R_4$ functionality, and the counter anion X of the imidazolium salt may be modified to improve the lipophilicity of compound. The $X^-$ counter anion may be from halides, carbonate, acetate, phosphate, hexafluorophosphate, tetrafluoroborate, nitrate, methylsulfate, hydroxide and sulfate. Each R group ($R_1$, $R_2$, $R_3$ and $R_4$), separately or in combination, can be selected from hydrogen, $C_1$ to $C_{12}$ alkyl, $C_1$ to $C_{12}$ substituted alkyl, $C_1$ to $C_{12}$ alkoxy, $C_1$ to $C_{12}$ cyclo alkyl, $C_1$ to $C_{12}$ substituted $C_1$ to $C_{12}$ cyclo alkyl, $C_1$ to $C_{12}$ alkenyl, $C_1$ to $C_{12}$ cycloalkenyl, $C_1$ to $C_{12}$ substituted cycloalkenyl, $C_1$ to $C_{12}$ alkynyl, $C_1$ to $C_{12}$ aryl, $C_1$ to $C_{12}$ substituted aryl, $C_1$ to $C_{12}$ arylalkyl, $C_1$ to $C_{12}$ alkylamine, $C_1$ to $C_{12}$ substituted alkylamine, $C_1$ to $C_{12}$ alkylpentose phosphate, $C_1$ to $C_{12}$ phenols, and $C_1$ to $C_{12}$ esters. The selection of $R_1$, $R_2$, $R_3$, and $R_4$ functionality is desirable in some of its pharmaceutical applications.

Purines are also being examined as carbene precursors for carrying silver. Of particular interest is guanine, one of the nucleobases in DNA. Guanine 91 has a ring system similar to that of caffeine compound represented by Formula 95. Since guanine is non-toxic it seems reasonable that 7,9-dimethylguanine would have low toxicity. This makes the dimethyl guanine ligand very attractive for cystic fibrosis research because we are looking for non-toxic as well as small ligands to serve as carriers for silver cations.

Dimethylation of guanine (see Formula 91) with dimethylsulfate followed by treatment with ammonium hydroxide gives the water insoluble 7,9-dimethylguanine zwitterion compound represented by Formula 92. Addition of HBr to the zwitterion compound represented by Formula 92 yields the bromide salt of Formula 93. The bromide salt is soluble in water and is precipitated out using THF. The silver complex is formed by suspending the bromide salt in DMSO, adding $Ag_2O$ to the solution and heating at 60° C. to 80° C. for about 6 hours.

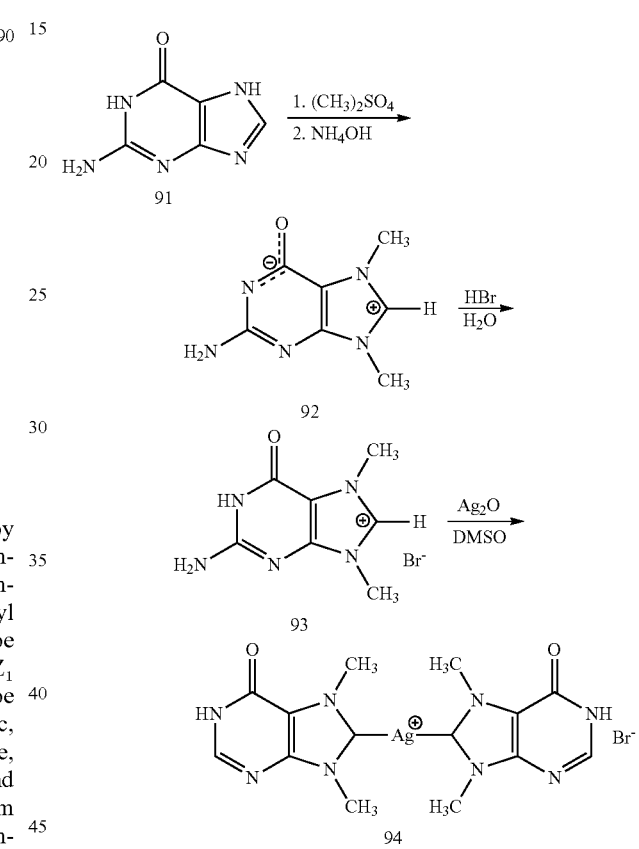

Xanthines have been used for a number of years as bronchodilators for the treatment of airway obstructions in cystic fibrosis patients. Because xanthines contain imidazole rings we assumed it should be possible to alkylate them to form imidazolium cations and eventually silver carbene complexes. Because of their use as bronchodilators we also assumed that their methylated derivatives would be relatively nontoxic. Probably the most well know of the xanthines is the caffeine compound represented by Formula 95. We have investigated the alkylation of caffeine to form methylated caffeine and the formation of silver carbene complexes using caffeine as the carbene precursor. Methylated caffeine has proven to be even less toxic than caffeine.

The methyl sulfate salt of methylated caffeine, 1,3,7,9-tetramethylxanthanium, represented by Formula 96a is produced by the reaction of the caffeine compound represented by Formula 95 with dimethyl sulfate in nitrobenzene. Anion exchange using $NH_4PF_6$ in water results in the compound represented by Formula 96b.

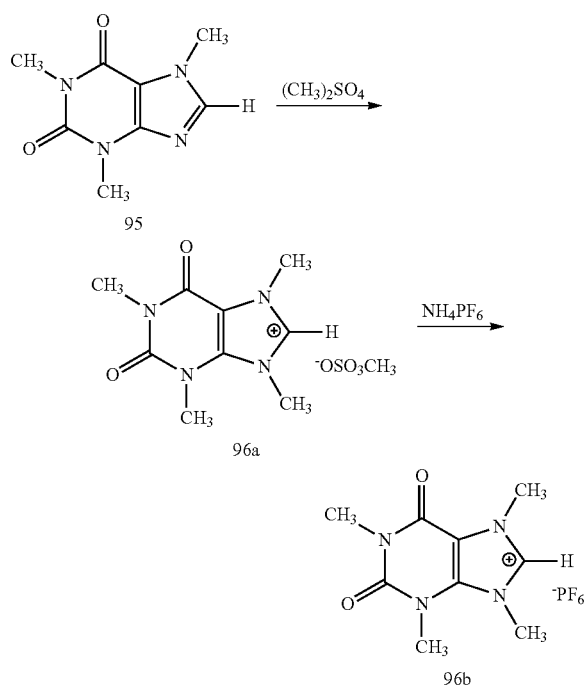

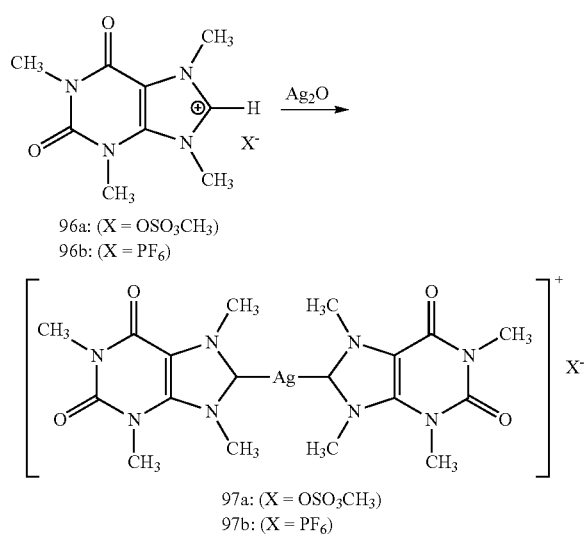

Ligand 96a is water soluble and reacts with Ag$_2$O in water to give the complex represented by Formula 97a. Formula 97a is stable in water for five days. The lack of C—$^{107}$Ag and C—$^{109}$Ag couplings suggests fluxional behavior on the $^{13}$C NMR timescale as observed with many silver(I) complexes. Similarly, Formula 96b reacts with Ag$_2$O in DMSO to form the compound represented by Formula 97b, which has been structurally characterized by X-ray crystallography. The thermal ellipsoid plots (TEP) of the cationic portions of Formulas 96b and 97b are shown below.

Caffeine, 1,3,7-trimethylxanthine, is one of the xanthine derivatives that are generally used in medicines as diuretics, central nervous system stimulants and inhibitors of cyclic adenosine monophosphate (c-AMP) phosphodiesterase. 1,3,7,9-tetramethylxanthinium iodide (methylated caffeine), an imidazolium salt, was synthesized using modified literature procedures and characterized by $^1$H, $^{13}$C NMR, mass spectrometry and X-ray crystallography.

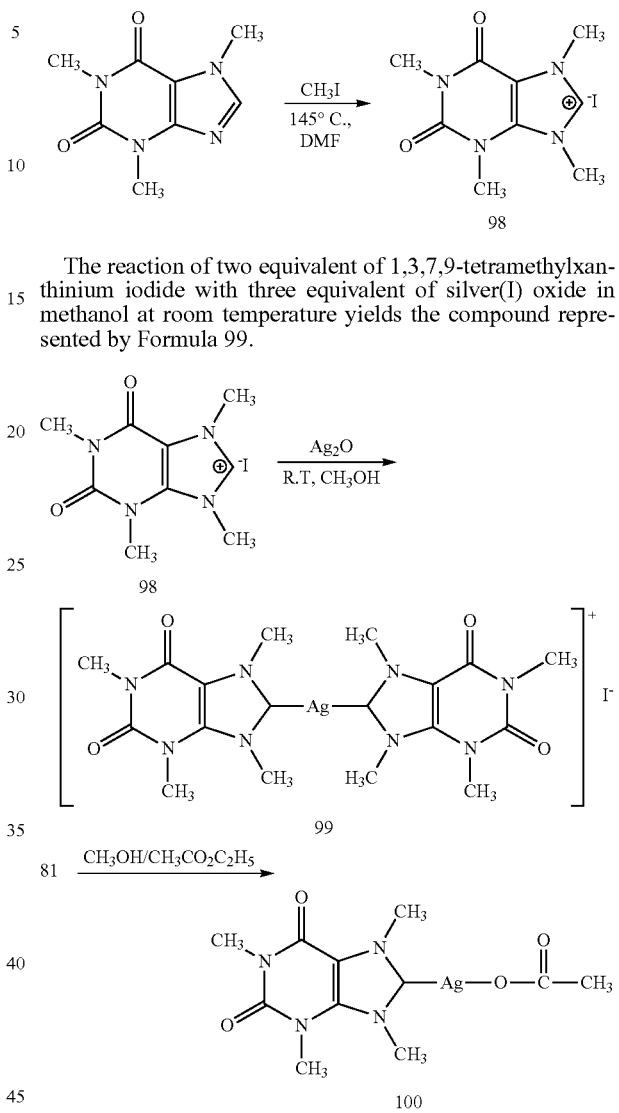

The reaction of two equivalent of 1,3,7,9-tetramethylxanthinium iodide with three equivalent of silver(I) oxide in methanol at room temperature yields the compound represented by Formula 99.

The crystallization of the compound represented by Formula 99 in a mixture of methanol and ethyl acetate yields the compound represented by Formula 100, a colorless crystal, soluble in water and air stable. The compounds represented by Formulas 99 and 100 were characterized by $^1$H, $^{13}$C NMR, and mass spectrometry. X-ray crystallography was used to confirm the molecular structure of the compound represented by Formula 100 with the thermal ellipsoid plot show above. The antimicrobial properties of the compound represented by Formula 100 have been evaluated using both the filter disk test and the standard MIC technique. The compound represented by Formula 100 was found to have effective antimicrobial activity on *S. aureus, P. aeruginosa*, and *E. coli*. The dose-response effect on the compound represented by Formula 98 was assessed to determine the toxicity of the compound on rats. The toxicity study, is a standard protocol used to determine the lethal dose required to kill half (LD 50) of the animals (rats). The LD 50 assessment on the compound represented by Formula 98 was 2.37 grams per kilogram of rat. The protocol used in this study was approved by the Institutional Animal Care and Use Committee (IACUC), University of Akron.

The delivery methods for administering an effective amount of transition metal complexes of N-heterocyclic carbenes for in-vitro and in-vivo medicinal application consist of aerosol, biodegradable polymers, polymeric micelles, hydrogel types materials, dendrimers, and modified C-60 fullerenes.

The reaction shown resulting in the silver carbene complex represented by Formula 202 is similar in nature to the silver carbene complex represented by Formula 100. The compound represented by Formula 202 is an additional silver complex of xanthine derivative, namely 7-(2,3-dihydroxypropyl)theophylline silver(I) complex. The compound represented by Formula 202 is a derivative of theophylline complexed with Ag (I) that has a $K_{sp}$ of 82 mg/mL (attributable to the hydroxyl group), and is stable in solid form for periods of a couple months. Synthesis of the compound represented by Formula 202 is adaptable to large scale production.

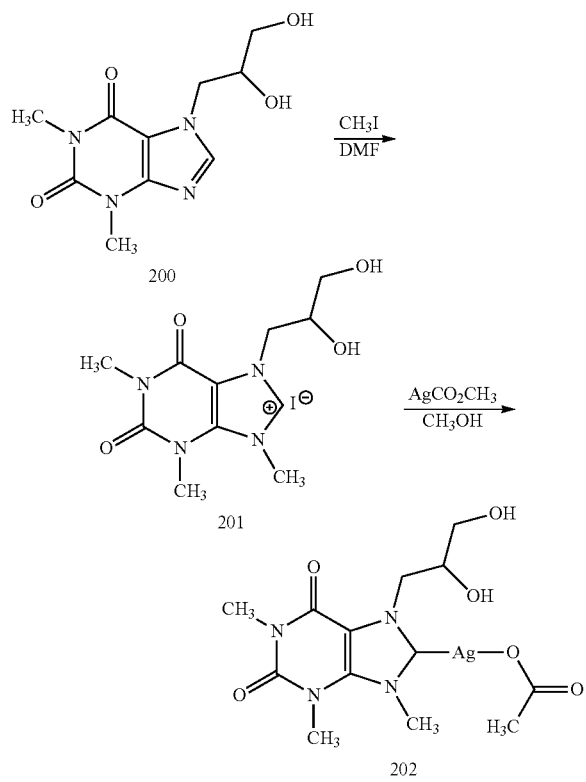

The imidazolium salt 1,3,9-trimethyl-7-(2,3-dihydroxypropyl)xanthenium iodide represented by Formula 201 is obtained by reacting 7-(2,3-dihydroxypropyl)theophylline (Formula 200) with methyl iodide in dimethylformamide. The imidazolium salt represented by Formula 201 reacts with silver acetate in methanol to yield the N-heterocyclic carbene silver(I) acetate complex (Formula 202), which is a white solid in 34% yield (structure confirmed by X-ray crystallography). The compound represented by Formula 202 is water soluble ($K_{sp}$=82 mg/mL) and is stable for at least 7 days in water by NMR. As the compound represented by Formula 202 decomposes to release $Ag^+$ thereby regenerating the cationic portion of the compound of Formula 201. The imidazolium cation portion of the compound represented by Formula 201 has an $LD_{50}$ in rats of >2.0 g/kg in preliminary studies.

The compound represented by Formula 202 has a shelf life of several months at room temperature. Each portion of the compound represented by Formula 202 can be readily reconstituted in sterile water to form a clear, colorless solution with a concentration of 10 mg/mL.

In addition to the imidazole ring portion that is converted into a carbene for binding metals, the feature common to the compounds represented by Formulas 100, 202 and the generic form of 56 is the presence of a bis-amide ring on the "backside" of the imidazole-carbene portion. This bis-amide ring is electron withdrawing. Silver acetate carbene complexes that do not contain electron-withdrawing groups in the ring are not as stable in water as the compounds represented by Formulas 100 and 202.

The minimum inhibitory concentrations (MIC) of the silver carbene compound represented by Formula 202 for a panel of E-coli from a variety of sources was determined (*Escherichia coli* being the leading cause of urinary tract infections). Strains influenced included the sequenced cystitis strain UTI89 and pyelonephritis strain CFT073; the sequenced laboratory *E. coli* strain MG1655; and seven strains from patients with acute or recurrent UTIs or asymptomatic bacteriuria. Overnight Luria broth (LB) cultures of these strains were sub-cultured 1:100, grown 2 to 3 hours to $OD_{600nm}$=0.4, and diluted 1000-fold in fresh LB. One hundred μL of each suspension was added to 100 μL of a range of dilutions of the compound represented by Formula 202 in wells of a 96-well plate. After 16 hours static incubation at 37° C., MICs were assessed visually and by quantitative absorbance measurement in a microplate reader at 600 nm. The MIC of the compound represented by Formula 202 against this panel of strains was generally 2 to 4 μg/mL, similar to that observed against *P. aeruginosa* and *Burkholderia* species.

A prerequisite for a topical biocide is that it confers acceptable toxicity to the tissue(s) of interest. In vitro toxicity of the compound represented by Formula 202 has been studied using the bladder carcinoma-derived T24 epithelial cell line (ATCC HTB-4). T24 cells were grown in RPMI 1640 medium available from Life Technologies (Carlsbad, Calif.) supplemented with 10% fetal bovine serum available from Sigma (St. Louis, Mo.), seeded into 24-well plates, and grown to confluence over 48 hours. Cells were washed with sterile phosphate buffered saline (PBS) and fresh warmed medium was added, either alone or containing the compound represented by Formula 202 (added to the medium at the start of the experiment to minimize premature liberation of $Ag^+$ from the compound represented by Formula 202) at concentrations between 5 and 50 μg/mL. After incubation for 1 to 2 hours, cells were released by treatment with 0.05% trypsin −0.02% EDTA, suspended in sorting buffer, stained with propidium iodide, and subjected to flow cytometry on a FACS Calibur instrument available from Becton Dickinson (Piscataway, N.J.). Our initial experiments demonstrate that loss of viability is ~5% after 1 h of treatment with 202 at 5 μg/mL and approximately 11% after 2 hours of such treatment.

Additional work has explored the addition of electron-withdrawing groups on the "backside" of the carbene moiety, which provides augmented stability to sodium, chloride, and other ions. Deprotonation of the compound represented by Formula 205 with potassium hydroxide followed by double methylation with methyl iodide gives the N-heterocyclic carbene compound represented by Formula 206. The bis(NHC) silver(I) complex represented by Formula 208 was formed from the reaction of the nitrate salt compound represented by Formula 207 with an excess of silver(I) oxide in acetonitrile.

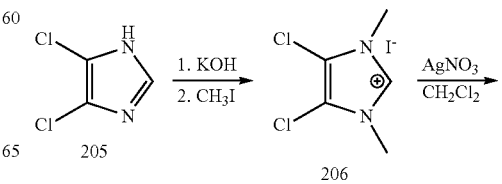

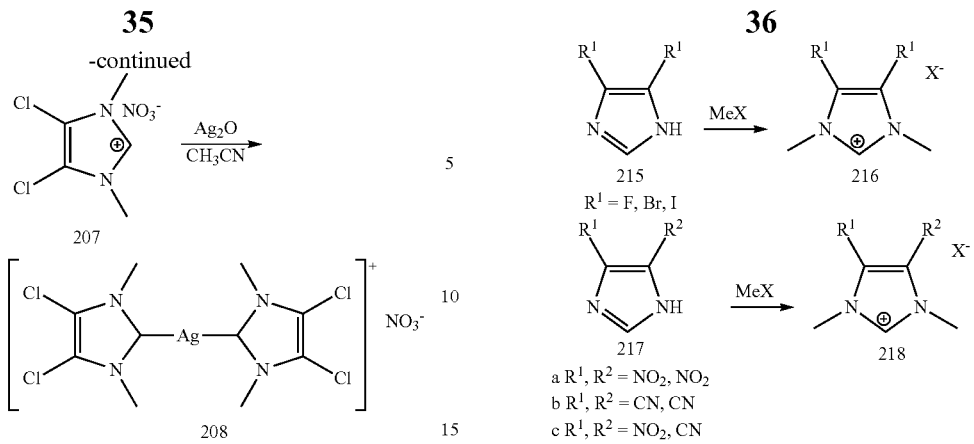

The bis(NHC) silver(I) complex, Formula 210, with an iodide anion was added to 0.9% sodium chloride solution (equivalent to physiological serum Na$^+$ concentration). The solution was decanted and the resulting precipitate was dissolved in acetone. Slow evaporation of acetone yield white crystals of a compound represented by Formula 211 that show bridging chlorides and a silver NHC bond still intact. The stability of the compound represented by Formula 211 to physiological concentrations of sodium chloride is unprecedented. In addition to stabilizing silver NHCs to water, the presence of electron-withdrawing groups on the imidazole ring can greatly enhance their stability to physiological sodium chloride. This type chemistry is particularly suited for use in the urinary tract, where urinary osmolality in humans may vary from 300 to 1200 mOsm/L.

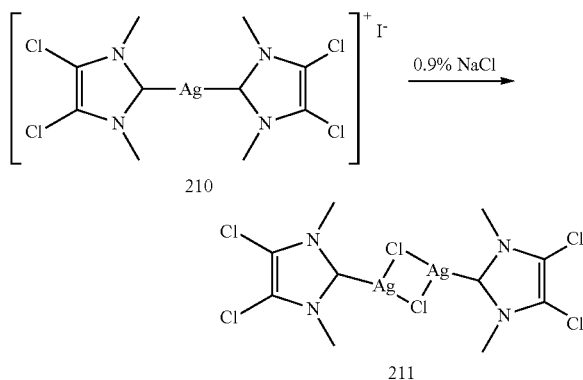

As stated above, the major advantage of SCs over earlier silver compounds is their stability and solubility in water. The addition of electron-withdrawing groups on the "backside" of the carbene component provides augmented stability to ionic strength, such as might be found in the urinary tract.

The 4,5-dihaloimidazoles, Formula 215, were also explored for their ability to form stable silver NHC complexes. The imidazolium salt represented by Formula 216 is synthesized using the appropriate methylating agents. Imidazole starting materials with other electron-withdrawing groups such as nitro and cyano groups, Formula 217, are examined. The dinitro and dicyano analogs of the compound represented by Formula 217 are commercially available and synthesis of the cyano-nifro analog is known. The imidazolium salts of these compounds, Formula 218, are synthesized according to the general procedure outlined as before. The compounds represented by Formulas 216 and 218 are then be combined with silver acetate and silver oxide to form new silver carbene using procedures discussed above.

The delivery methods for administering an effective amount of silver complexes of N-heterocyclic carbenes for in-vitro and in-vivo medicinal application consist of (or include) aerosol, biodegradable polymers, polymeric micelles, hydrogel types materials, dendrimers, and modified C-60 fullerenes. The silver carbene complexes are used in an amount from 0.01 μg to 600 mg. The preferred delivery method for treating urinary tract infections using silver carbene complexes involves dissolving the silver carbene complex into a fluid such as, but not limited to, water or saline. Water and saline are preferred due to their compatibility with the human body, but other fluids can be used as well depending upon the application. The silver carbene complex solution is instilled into the urinary bladder via an instrument such as, but not limited to, a urinary catheter. A normal sized urinary bladder in an adult human is 500 to 600 mL. The preferred amount of fluid used in treatment of urinary tract infections is 1 to 600 mL, another preferred range is 25 to 450 mL, and another preferred range is 80 to 300 mL. The preferred concentration of the silver carbene complex in fluid is in the range of 0.01 to 1000 μg/mL, another preferred range is 0.5 to 100 μg/mL and another preferred range is 1 to 25 μg/mL.

Regarding urinary tract infections the terms treating and/or treatment include resolving an existing urinary tract infection and/or pre-treating a bladder to prevent the initiation of a urinary tract infection. Such pretreatments would benefit patients at-risk for urinary tract infections. Pre-treating the bladder for a urinary tract infection involves the same method of filling the bladder as treatment, but with less frequency. For example, patients practicing clean intermittent catheridization would adhere to a periodic schedule such as but not limited to once a month, once a week or once a day.

In order to demonstrate the practice of the present invention, two N-heterocyclic carbenes represented by Formulas 101 and 102 were synthesized and tested for antimicrobial properties as described below. The compounds can be shown with reference to Formula 4:

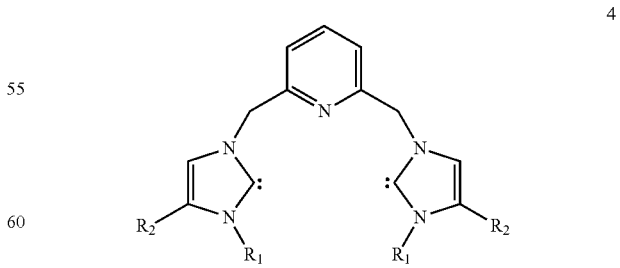

where $R_1$ is a hydroxyethyl or hydroxypropyl group and $R_2$ is a hydrogen atom. These carbenes 101 and 102 were synthesized by reacting 2,6-bis-(imidazolmethyl)pyridine with either 2-iodoethanol or 3-bromopropanol to provide compounds of Formulas 101 and 102.

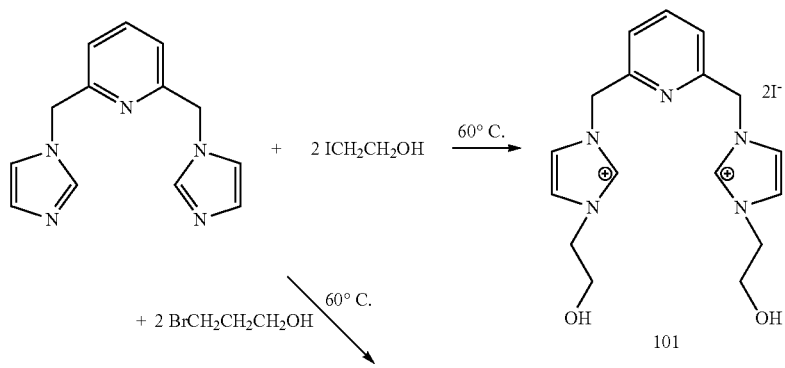

101

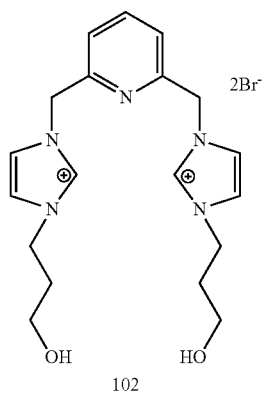

102

The IR spectra for these compounds show an O—H stretching band vibration, 3325 cm$^{-1}$. FAB-MS spectra obtained from these compounds in nitrobenzyl matrices showed [51][I]$^+$ ($C_{17}H_{23}N_5O_2I$) at m/z 456 and [52][I]$^+$ ($C_{19}H_{27}N_5O_2Br$) at m/z 436. These compounds readily react with Ag$_2$O to form the silver-bis(carbene) pincer complexes represented by Formulas 103 and 104 in high yield.

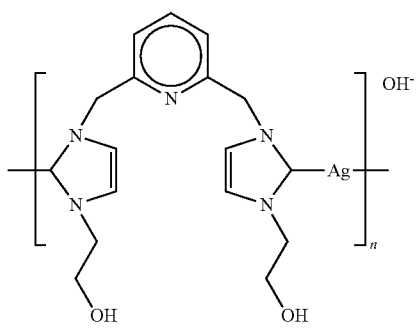

103

-continued

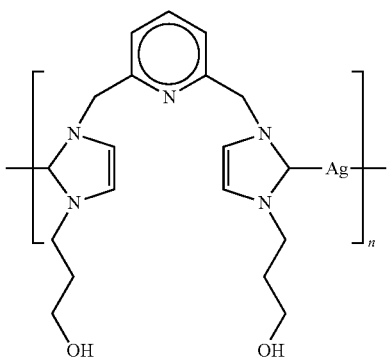

104

The formation of the compounds represented by Formulas 103 and 104 is confirmed by the loss of the imidazolium proton at 9.13 ppm, 9.36 ppm in the $^1$H NMR spectra of these compounds, and the appearance of a resonance at 181 ppm in the $^{13}$C NMR spectra of these compounds. Further evidence for the formation and structure of compound 103 is provided by X-ray crystallography.

Figure 1B:
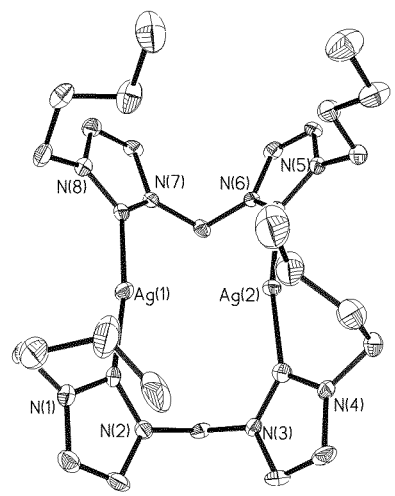

Colorless crystals of the compound represented by Formula 103 were obtained by slow evaporation of a methanol solution of the compound represented by Formula 103. Interestingly, the compound represented by Formula 103 undergoes complete anion exchange in aqueous methanol, replacing the iodide anions with hydroxide anions. In the solid state, the compound represented by Formula 103 exists as a one-dimensional linear polymer as shown in FIG. 1. FIG. 1 is a thermal ellipsoid plot of the compound represented by Formula 103 with the thermal ellipsoid drawn at a 30 percent probability level. The hydrogen atoms have been omitted from FIG. 1 for clarity.

The geometry at the silver atoms is nearly linear with a C5-Ag1-C15 bond angle of 174.7(4)°, and Ag1-C15, and Ag1-C15 bond distances of 2.108(11) Angstroms and 2.060 (13) Angstroms, respectively. Mass spectroscopy suggests that in solution and in the gas phase, the compound represented by Formula 103 exists as monomer, whereas X-ray crystallography shows that the compound represented by Formula 103 is polymeric in the crystal.

Figure 2:
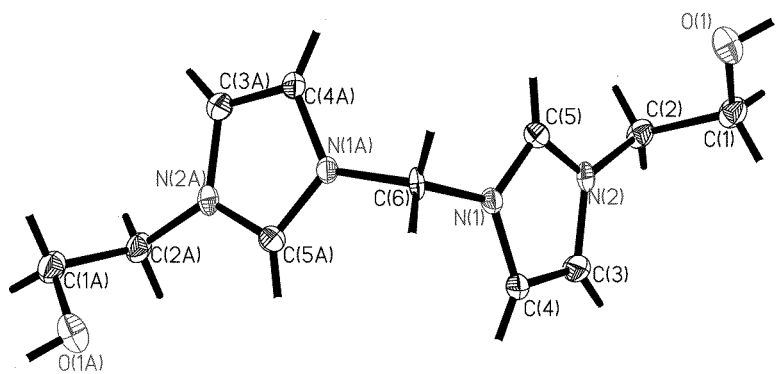
FIG. 2 is a thermal ellipsoid plot of the water soluble diol shown as Formula 13.
Figure 3:
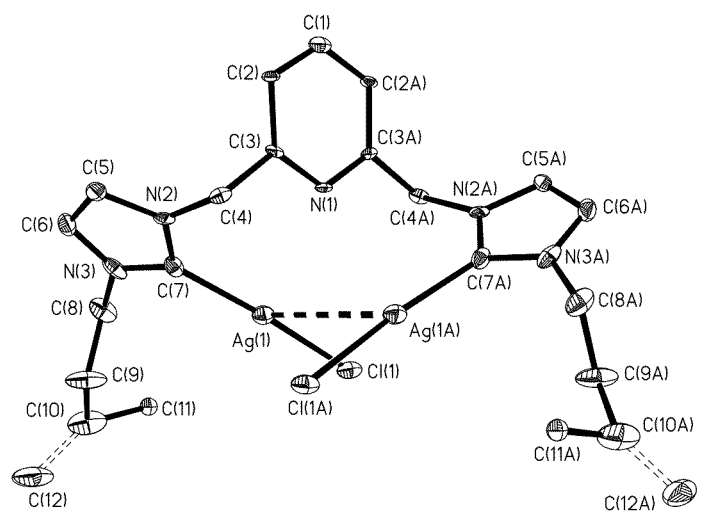
FIG. 3 is a thermal ellipsoid plot of the silver carbene complex shown as Formula 17.
Figure 4:
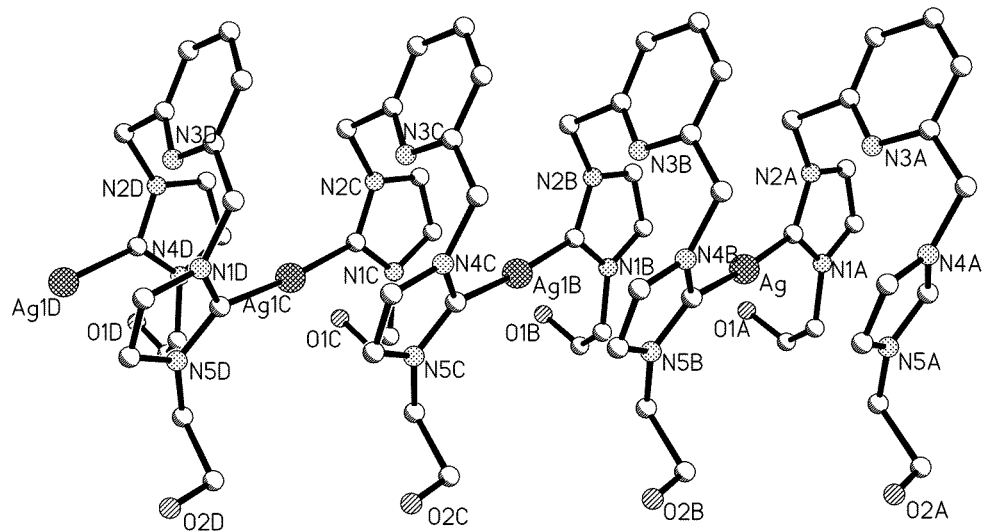

An anion exchange reaction of the compound represented by Formula 103 with aqueous ammonium hexafluorophosphate results in the formation of the compound represented by Formula 105. In the solid state, the compound represented by Formula 105 exists as a dimer, as shown in FIG. 2. FIG. 2 is a thermal ellipsoid plot of the compound represented by Formula 105 with the thermal ellipsoid drawn at a 30 percent probability level. The hydrogen atoms have been omitted from FIG. 2 for clarity. The geometry of the silver atoms are nearly linear with C32-Ag1-O5)(175.7(4)°, C22-Ag2-C17) (174.6(3)° bonds angles, and Ag1-C32 (2.070(9) Angstroms), Ag1-O5 (2.091(9) Angstroms), Ag2-C22 (2.064(9) Angstroms), Ag2-C17 (2.074(8) Angstroms) bond lengths. The nature of the anions is significant to the structural changes of the compound represented by Formula 103 versus the compound represented by Formula 105, and the choice of anion has a pronounced effect on the solubility of these compounds. For example, the compound represented by Formula 103 is soluble in aqueous media whereas the compound represented by Formula 105 is not. Table 1 gives a summary of the crystal data of both of these compounds.

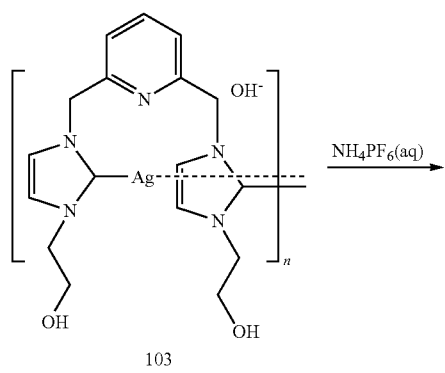

103

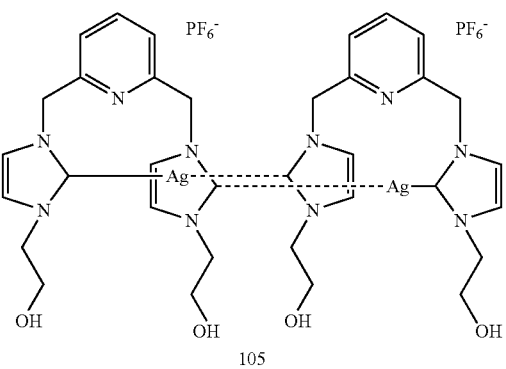

105

TABLE 1

| | 103, $C_{17}H_{22}N_5O_3Ag$ | 105, $C_{34}H_{42}N_{10}O_4AgP_2F_{12}$ |
|---|---|---|
| Empirical Formula | 103, $C_{17}H_{22}N_5O_3Ag$ | 105, $C_{34}H_{42}N_{10}O_4AgP_2F_{12}$ |
| Formula Weight | 434.0735 | 868.1481 |
| Temperature (K) | 100 | 100 |
| Wavelength (Å) | 0.71073 | 0.71073 |
| Crystal system, space group, Z | Orthorhombic, P2(1)2(1)2(1), 4 | Monoclinic, P2(1)/c, 8 |
| Unit cell dimensions | | |
| a (Å) | 4.5586(17) | 10.9448(14) |
| b (Å) | 14.900(6) | 22.885(3) |
| c (Å) | 29.923(12) | 17.729(2) |
| α (°) | 90 | 90 |
| β (°) | 90 | 92.196(2) |
| γ (°) | 90 | 90 |
| V (Å3) | 2032.5(14) | 4437.4(10) |
| Dcalc (Mg/m3) | 1.422 | 1.737 |
| Absorption coefficient (mm-1) | 1.010 | 1.055 |
| Theta range for data collection (°) | 1.36 to 24.99 | 1.45 to 25.00 |
| Reflections collected/unique | 6300/3506 [R(int) = 0.0650] | 20811/7757 [R(int) = 0.0437] |
| Goodness-of-fit on F2 | 1.034 | 1.058 |
| Final R indices [I > 2 σ (I)] | 0.0655 | 0.0956 |
| R indices (all data) | 0.1410 | 0.2491 |
| Largest difference peak and hole (e Å-3) | 0.954 and -0.875 | 2.069 and -1.230 |

The usefulness of the compounds represented by Formulas 103 and 55 as antimicrobial agents was evaluated. The standard agar plates overlay method was used to obtain the sensitivity data as presented in Table 2. In this test, a filter paper disc of 6 mm diameter was soaked with 20 μL of a silver compound of known concentration, and placed over a lawn of an organism in the agar plate. The diameter of the area in which growth of the organism is inhibited by the test solution was measured after an over night incubation as a measure of the relative antimicrobial activity of the silver compounds. The test organisms were *Escherichia coli*, *Staphylococcus aureus*, and *Pseudomonas aeruginosa*. Silver nitrate was the reference standard used, while the compounds represented by Formulas 101 and 102 served as a negative controls.

TABLE 2

Antimicrobial Activity of Silver Compounds

| Tested compounds | Ag+ (μg/mL) | E. coli | S. aureus | P. aeruginosa |
|---|---|---|---|---|
| | | Diameter of Inhibited Area (mm) | | |
| AgNO$_3$ - 0.5% (w/v) | 3176 | 11.38 | 10.88 | 11 |
| Compound 103 - 1.31% | 3130 | 11.5 | 11 | 12 |
| Compound 105 - 1.42% | 3195 | 11.58 | 10.67 | 10.25 |
| Compound 103 - 0.50% | 1195 | 10.13 | 10 | 11.13 |
| Compound 105 - 0.50% | 1125 | 10 | 9 | 12 |
| Compound 101 - 0.50% | | 6 | 6 | 6 |
| Compound 102 - 0.50% | | 6 | 6 | 6 |

The data confirmed that compounds 103 and 105 have antimicrobial properties at a level comparable to silver nitrate as shown in Table 2. The pincer ligands, compounds 101 and 102, were found to have no antimicrobial activity.

The silver compounds were also tested according to the minimum inhibition concentration determination method (MIC). The MIC is a standard microbiological technique used to evaluate the bacteriostatic activity of antimicrobial agents. In this case, the MIC was based on the total amount of silver available and not on the concentration of silver ions. A 0.5 percent (w/v) solution of each of the silver compounds 103 and 105 was tested. On dissolving of the silver complexes in the culture medium (LB broth), a precipitate of AgCl was observed in all samples. The activity of a dilution series of the supernatant portion of the silver complex solutions was evaluated, with the addition of a constant volume of freshly grown organism (20 μL) per day. *Escherichia coli, Staphylococcus aureus*, and *Pseudomonas aeruginosa* were again used as the test organisms. The MIC was obtained by visual inspection of the cultures for growth(+) or no growth(−) as reported in Table 3. In Table 3, DF is the dilution factor. From the results, it can be concluded that compounds 103 and 105 are less bound to chloride ion than silver nitrate, due to the stability of the Ag—C donor ligand bond. Thus, compounds 103 and 105 show better antimicrobial activity than silver nitrate. This is a desirable property of compounds 103 and 105, when considering silver compounds for in vivo application. It may be noted that although equal weights of silver compounds were used, the amount of silver ions released by compounds 103 and 105 is about 2.7 times lower than the amount of silver ions released by silver nitrate.

TABLE 3

MIC Results of Supernatants of Silver Compounds (less silver chloride)

| Test Ag compounds | Ag (ul/ml) | E. coli | | P. aeruginosa | | S. aureus | |
|---|---|---|---|---|---|---|---|
| | | Day 1 | Day 2 | Day 1 | Day 2 | Day 1 | Day 2 |
| 103 | 1186 | − | − | − | − | − | − |
| ×1DF | | − | + | − | − | − | + |
| ×2DF | | − | + | − | + | + | |
| ×3DF | | + | | + | | + | |
| ×4DF | | + | | + | | + | |
| 105 | 1125 | − | − | − | − | − | − |
| ×1DF | | − | + | − | + | − | + |
| ×2DF | | − | + | − | + | + | |
| ×3DF | | + | | + | | + | |
| ×4DF | | + | | + | | + | |
| AgN03 | 3176 | − | + | − | + | + | |
| ×1DF | | + | | + | | + | |
| ×2DF | | + | | + | | + | |
| ×3DF | | + | | + | | + | |
| ×4DF | | + | | + | | + | |

While not wishing to condition patentability on any particular theory, it is believed that the activity and stability of compounds 103 and 105, as well as their solubility in water, may be attributed to the relatively slow decomposition of Ag—C donor ligand bond over time to silver metal and silver ion.

When the MIC test was repeated as described above except in the presence of insoluble silver chloride, the activity of the silver compounds was enhanced, with silver nitrate performing better as shown in Table 4. It has been previously reported that the presence of chloride contributes to the toxicity of silver in sensitive strains of organisms.

TABLE 4

Effect of Chloride (as Silver Chloride) in the Bactericidal Activity of Silver Compounds

| Tested Ag compounds | E. coli (Days) | | | | | | P. aeruginosa (Days) | | | | | | S. aureus (Days) | | | | | |
|---|---|---|---|---|---|---|---|---|---|---|---|---|---|---|---|---|---|---|
| (% w/v) | 1 | 2 | 3 | 4 | 5 | 6 | 1 | 2 | 3 | 4 | 5 | 6 | 1 | 2 | 3 | 4 | 5 | 6 |
| 103 | | | | | | | | | | | | | | | | | | |
| 0.50 | − | − | − | − | − | − | − | − | − | − | − | − | − | − | − | − | − | − |
| 0.25 | − | − | − | − | − | − | − | − | − | − | − | − | − | − | − | − | − | − |

TABLE 4-continued

Effect of Chloride (as Silver Chloride) in the Bactericidal Activity of Silver Compounds

| Tested Ag compounds | E. coli (Days) | | | | | | P. aeruginosa (Days) | | | | | | S. aureus (Days) | | | | | |
|---|---|---|---|---|---|---|---|---|---|---|---|---|---|---|---|---|---|---|
| (% w/v) | 1 | 2 | 3 | 4 | 5 | 6 | 1 | 2 | 3 | 4 | 5 | 6 | 1 | 2 | 3 | 4 | 5 | 6 |
| 0.12 | − | − | − | − | − | − | − | − | − | − | − | − | − | − | − | − | − | − |
| 0.06 | − | − | − | − | − | − | − | − | − | − | − | − | − | − | − | − | − | − |
| 0.03 | − | − | + | − | − | − | − | − | + | − | − | − | − | + | − | − | − | − |
| 105 | | | | | | | | | | | | | | | | | | |
| 0.50 | − | − | − | − | − | − | − | − | − | − | − | − | − | − | − | − | − | − |
| 0.25 | − | − | − | − | − | − | − | − | − | − | − | − | − | − | − | − | − | − |
| 0.12 | − | − | − | − | − | − | − | − | − | − | − | − | − | − | − | − | − | − |
| 0.06 | − | − | − | − | − | − | − | − | − | − | − | − | − | − | − | − | − | − |
| 0.03 | − | − | + | − | − | − | − | − | + | − | − | − | − | + | − | − | − | − |
| AgNO$_3$ | | | | | | | | | | | | | | | | | | |
| 0.50 | − | − | − | − | − | − | − | − | − | − | − | − | − | − | − | − | − | − |
| 0.25 | − | − | − | − | − | − | − | − | − | − | − | − | − | − | − | − | − | − |
| 0.12 | − | − | − | − | − | − | − | − | − | − | − | − | − | − | − | − | − | − |
| 0.06 | − | − | − | − | − | − | − | − | − | − | − | − | − | − | − | − | − | − |
| 0.03 | − | − | − | + | − | − | − | − | + | − | − | − | − | − | + | − | − | − |

The minimum lethal concentration was determined to evaluate the bactericidal properties of the compounds represented by Formulas 103 and 105. The clear (no growth) portion of the culture media with the lowest Ag compound concentration was used, by streaking 0.01 mL of the solution on agar plate using a sterilized loop followed by incubation at 37° C. for 24 to 48 hours. The colonies were visually counted, with the end point of the minimum bactericidal concentration (MBC) as no growth on the agar plate. The test compounds showed an improved bactericidal effect compared to silver nitrate up to the seventh day of incubation and MBC test, with no growth observed after the tenth day of incubation and testing for the silver compounds. This is despite the fact that freshly grown organisms were added each day to the culture media containing the silver compounds throughout the incubation period. The bactericidal and bacteriostatic properties of 103 and 105 are believed to be due to the slow decomposition of the Ag—C donor (carbene) ligand bond over time to silver metal, silver ion, AgCl and to their solubility in water.

The alkanol N-functionalized silver carbene complexes represented by Formulas 103 and 105 are soluble in aqueous media. In addition, they have proved to be useful antimicrobial agents, and their solubility in water makes them excellent silver compounds that can be of use for in vivo application. The solubility and stability of silver complexes in chloride solution have been key factors that have limited the use of silver complexes for in vivo application.

According to another aspect of the present invention, a silver(I) imidazole cyclophane gem diol complex 106 $[Ag_2C_{36}N_{10}O_4]^{2+}$ $2(x)^-$, where x=OH$^-$, $CO_3^{2-}$ was synthesized. The MIC test showed that the antimicrobial activity of the aqueous form of 106 is 2 fold less effective than 0.5% AgNO$_3$, with about the same amount of silver. The antimicrobial activity of 106 was enhanced when encapsulated into Tecophilic® polymer by electrospinning (technique) to obtain mats made of nano-fibers. The fiber mats release aggregates of silver nanoparticles and sustained the antimicrobial activity of the mats over a long period of time. The rate of bactericidal activity of the compound represented by Formula 106 was greatly improved by encapsulation, and the amount of silver used was much reduced. The fiber mat of the compound represented by Formula 106 with 75% (106/tecophilic) contained 2 mg of Ag, which is 8 times lower than 16 mg (0.5%) AgNO$_3$ and 5 times lower than silver sulfadiazine cream 1% (10 mg). The fiber mat was found to kill S. aureus at the same rate as 0.5% AgNO$_3$, with zero colonies on an agar plate and about 6 hours faster than silver sulfadiazine cream. Inoculums tested on and found effective are E. coli, P. aeruginosa, S. aureus, C. albicans, A. niger and S. cerevisiae. Transmission electron microscopy and scanning electron microscopy were used to characterize the fiber mats. The acute toxicity of the ligand (imidazolium cyclophane gem diol dichloride) was assessed by intravenous administration to rats, with an LD 50 of 100 mg/Kg of rat.

An electrospun fiber of the present invention can encapsulate a silver(I) N-heterocyclic carbene complex. The antimicrobial activity of silver(I)-N-pincer 2,6-bis(hydroxylethylimidazolemethyl)pyridine hydroxide, a water soluble silver (I) carbene complex 107, on some clinically important bacteria was described above. Compound 107 is an example of a compound that is sparingly soluble in absolute ethanol but completely soluble in methanol. The solubility of type 1 silver(I) carbene complexes in ethanol, was improved by varying the functionalized groups coupled to the nucleophilic end of the bis(imidazolmethyl)pyridine compound. Although embodiments wherein m=2 and m=3 are shown in Formula 107, m can have any positive integer value that is at least 1, and preferably, m has a value within the range of about 1 to about 4. Further, alternate starting materials or precursors described above may be used to produce a desired silver(I) carbene complex without departing from the scope of the present invention. The specific embodiments illustrated and described below are used for illustrative purposes in describing the present invention.

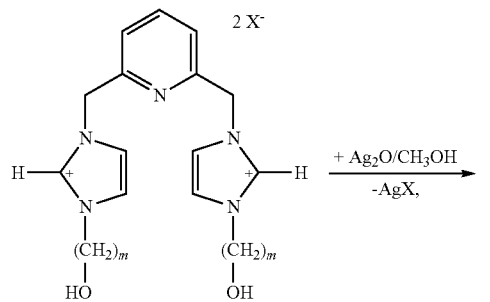

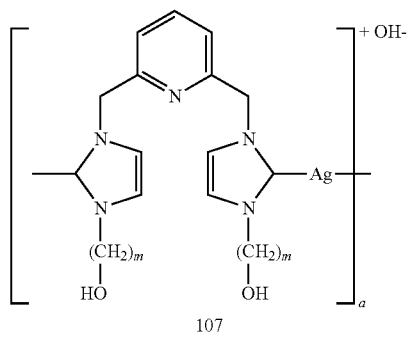

where (a) m=2 and (b) m=3.

Electrospinning is a versatile method used to produce fibers with diameters ranging from a few nanometers to over microns by creating an electrically charged jet of polymer solution or polymer melt, which elongates and solidifies. The resulting fibers can be used in filters, coating templates, protective clothing, biomedical applications, wound dressing, drug delivery, solar sails, solar cells, catalyst carriers, and reinforcing agents for composites.

The imidazolium (NHC) cyclophane gem-diol salt 108 can be prepared by reacting 2,6-bis(imidazolmethyl)pyridine with 1,3-dichloroacetone as shown below in Equation 2. The formation of the salt compound represented by Formula 108 as a gem-diol in preference to the carbonyl form is not expected with electron withdrawing groups present. Without being bound to theory, it is believed that the formation of the salt compound represented by Formula 108 as a gem-diol proceeded by acid-catalyzed process with the solution observed to be slightly acidic having a pH range of 5 to 6.

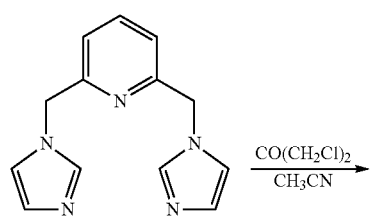

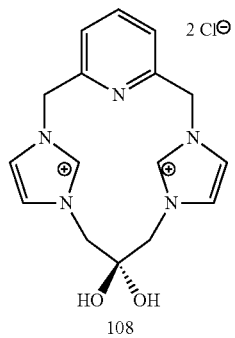

Figure 24:
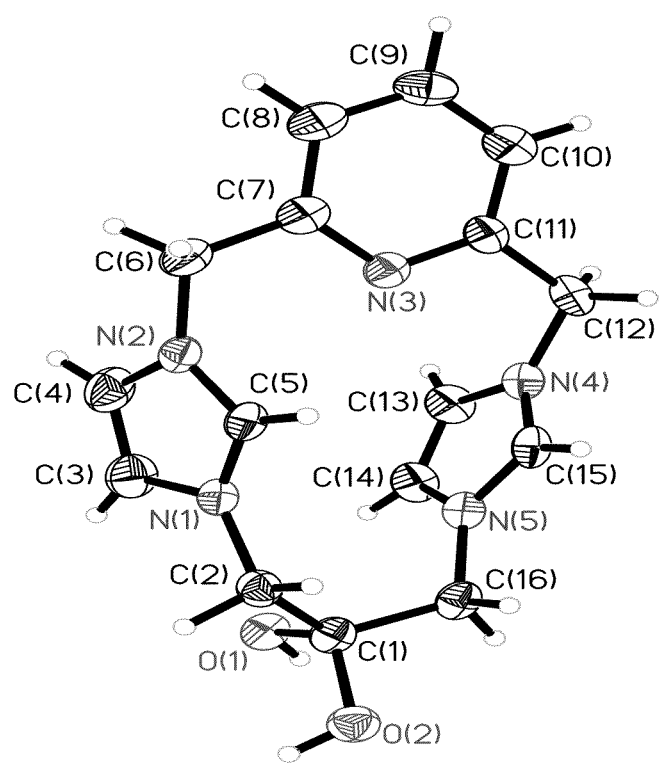
FIG. 24 is a thermal ellipsoid plot of the salt shown in Formula 108 with the thermal ellipsoid drawn at 50% probability level (the counter anions are omitted for clarity)

The $^1$H NMR spectra showed the presence of gem O—H as a broad peak at 7.65 ppm, and the absence of C=O in the salt compound represented by Formula 108 was observed in both $^{13}$C NMR and IR spectroscopy. The O—H stretching vibration was observed at 3387 cm$^{-1}$, while the C—O stretching at 1171 cm$^{-1}$ and $^{13}$C NMR chemical shift at 91 ppm. The x-ray crystallography further provided the evidence and structure of the compound represented by Formula 108 as shown in FIG. 24.

The combination of silver(I) oxide with the salt compound represented by Formula 108 in methanol according to the reaction scheme illustrated in Equation 3 results in the complex represented by Formula 106 as an air and light stable yellow solid in high yield, confirmed by the loss of the imidazolium proton at 9.35 ppm of the $^1$H NMR spectra. The proton NMR of the complex compound represented by Formula 106 showed a broad signal with complicated peaks that are not easily assigned. Again, without being bound to theory, this may be due to the fluxional behavior of the compound on the NMR time scale.

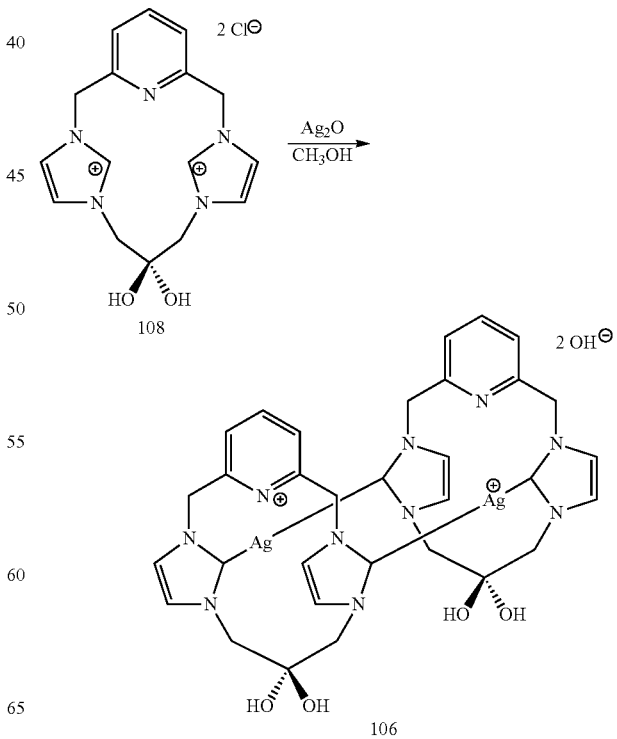

Figure 25:
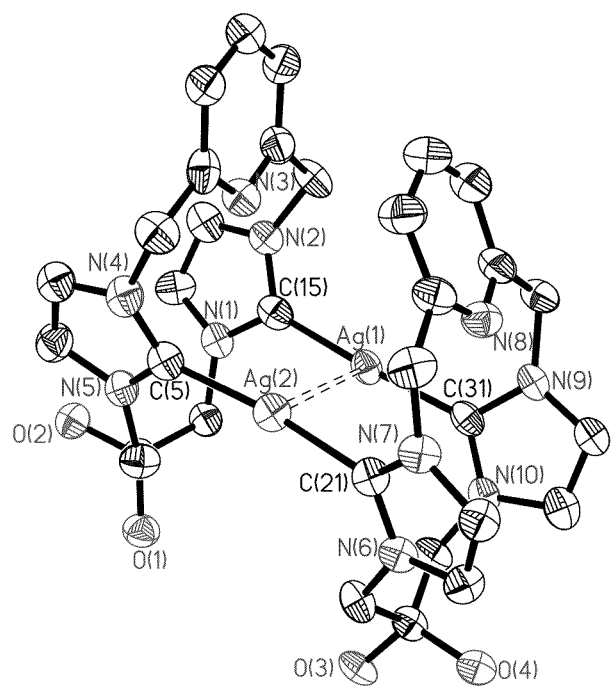
FIG. 25 is a thermal ellipsoid plot thermal ellipsoid plot of Complex 106 with the thermal ellipsoid drawn at 50% probability level (the counter anions are omitted for clarity)

The shift in the resonance signal of the imidazole carbon (NCN) from 138 ppm to downfield of the $^{13}$C NMR spectra at 184 and 186 ppm shows the rare coupling of the Ag—C bond. The large value of the Ag—C coupling constant ($J_{Agc}$=211 Hz) observed agreed with the reported range of 204 Hz to 220 Hz for $^{109}$Ag nuclei coupling. $^{109}$Ag coupling is commonly observed due to its higher sensitivity compared to the $^{107}$Ag. The x-ray crystallography confirms the structure of complex 106, which is shown in FIG. 25, with bond distances of Ag1-C15=2.085(5) Angstrom, Ag1-C31=2.077(5) Angstrom, Ag2-05=2.073(5) Angstrom and Ag2-C21=2.072 Angstrom. A weak Ag1-Ag2 interaction was observed with a bond length of 3.3751(10) Angstrom, longer than the commonly reported Ag—Ag bond range of 2.853-3.290 Angstrom, but shorter than the Van der waals radii for Ag—Ag of 3.44 Angstroms. In silver metal the Ag—Ag bond distance is known to be 2.888 Angstroms. The C—Ag—C bond angles are almost linear with C15-Ag1-C31 bond angle of 175.20(18)° and C21-Ag2-05 bond angle of 170.56(18)°.

Figure 26A:
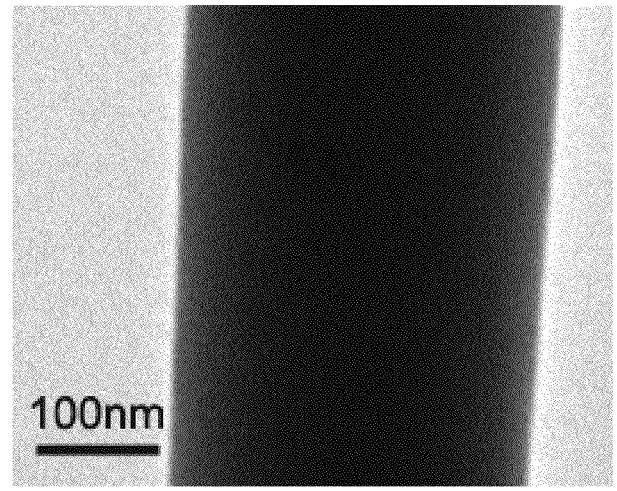
FIGS. 26*a* and 26*b* are electrospun fibers prepared from a mixture of Complex 106 and Tecophilic® at a weight ratio of 25 to 75, where FIG. 26*a* details as-spun fiber and FIG. 26*b* details silver particles formed by exposing the as-spun fiber to water.
Figure 26B:
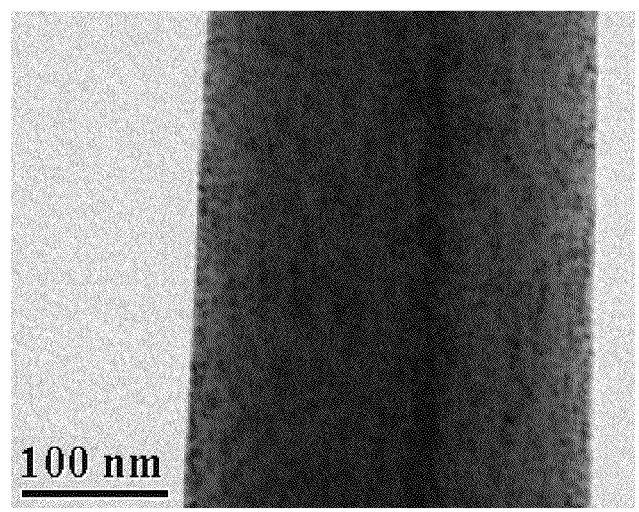
Figure 27A:
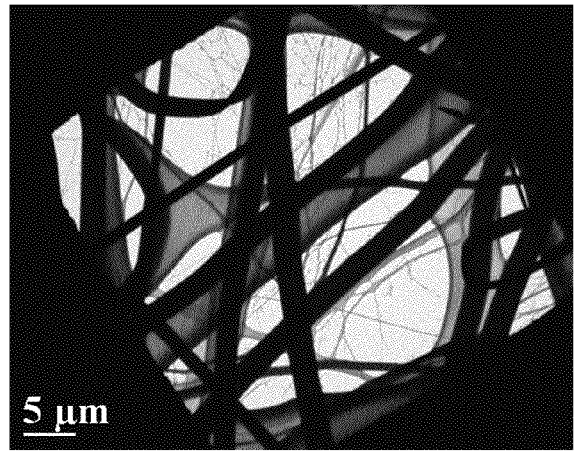
FIGS. 27*a* and 27*b* are TEM images showing the release of silver particles by exposing fibers of Complex 106 and Tecophilic® (weight ratio 50:50) to water vapor environment.
Figure 27B:
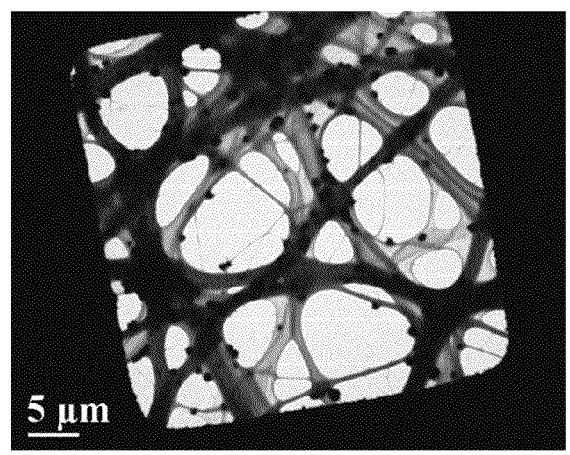

The electrospun fibers from Tecophilic® and silver complex were characterized by transmission electron microscopy (TEM) and scanning electron microscopy (SEM). No obvious phase separation was observed in as-spun fibers, shown in FIG. 26, which indicated a generally-uniform mixing of Tecophilic® and silver complex. The thickness of the fiber mat was measured by scanning electron microscopy (SEM) with pure Tecophilic® (100 micron), 25:75 silver complex 106/Tecophilic® (30 microns) and 75:25 complex 106/Tecophilic® (60 microns) respectively. The encapsulation of complex 106 by polymer retards the quick decomposition of silver complex into silver ions or particles in an aqueous media. The formation of silver particles at nanometer scale has been observed in the polymer matrix, when the electrospun fiber is exposed to water. Transmission electron microscopy studies showed that the activation of nanosilver particles in the fiber is a process that occurs gradually over a period of time. By exposing the as-spun fibers to water, complex 106 decomposed and release silver ions which aggregated into silver particles at nano-scale measurement. The formation of aggregates of silver particles has been observed within 30 minutes of exposure to water vapor (as shown in FIG. 27). The aggregation of the silver ions in the presence of water, with the aggregate adsorbed on the surface of the fibers is considered to be a simplified mechanism by which the fiber mat releases the active form(s) of the silver for its antimicrobial activity. The fiber of complex 106 is stable in light and air for months, but sensitive to an environment with very high humidity.

Figures 28A, 28B, 28C:
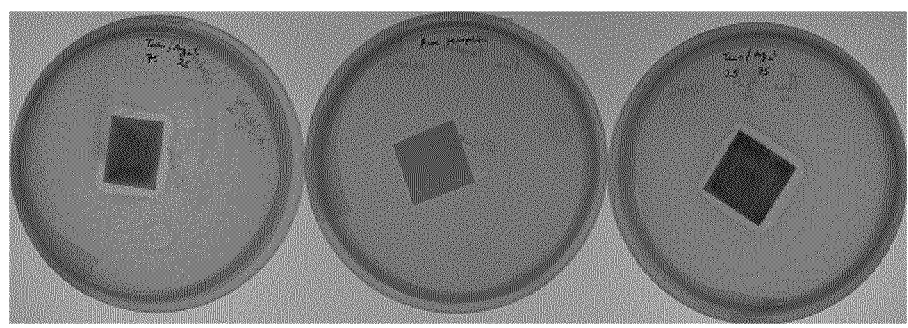
FIGS. 28*a*, 28*b* and 28*c* are images of the susceptibility test of the fiber mat encapsulating Complex 106, with bactericidal activity compared to pure Tecophilic® fiber mat, with FIG. 28*a* being an image of Complex 106/Tecophilic® (weight ratio 25:75), FIG. 28*b* being an image of pure Tecophilic®, and FIG. 28*c* being an image of Complex 106/Tecophilic® (weight ratio 75:25)

Bactericidal Effect:

Using a modified Kirby Bauer technique mats of electrospun Tecophilic® fiber encapsulating complex 106 and pure electrospun Tecophilic® fiber as control were placed on a lawn of organism in an agar plate and incubated overnight at 35° C. The inocula used were both Gram positive and Gram negative prokaryotes (*Escherichia coli, Pseudomonas aeruginosa*, and *Staphylococcus aureus*) of clinical interest. The fungi used were *Candida albicans, Aspergillus niger*, and *Saccharomyces cerevisiae*. The bactericidal activity showed a clear zone of inhibition within and around the fiber mat after an overnight incubation of the agar plate at 35° C. The fungicidal activity was observed after 48 hrs of incubation at 25° C. Pure Tecophilic® fiber mat as control showed no growth inhibition (see FIG. 28). No obvious difference was observed in the diameter of the cleared zone of inhibition around the fiber mat when the composition of the fiber mat was changed from 75% of complex 106 and 25% Tecophilic® to 25% of complex 106 and 75% Tecophilic®. The diameter of the zone of inhibition for the 75% (complex 106/Tecophilc®) fiber mat is 4.00 mm while that of 25% (complex 106/Tecophilc®) is 2.00 mm. The difference in diameter of the zone of inhibition between the two types of fiber mat has no linear relationship with the amount of silver (3:1 ratio) present in the two fiber mats. These result further shows the limitation of the Kirby Bauer technique as a quantitative tool to determine the antimicrobial activity of drugs. The diffusing ability of the silver ions might have been limited by the formation of secondary silver compounds. Ionic silver is known to undergo ligand exchange reactions with biological ligands such as nucleic acids, proteins, and cell membranes.

Figure 29:
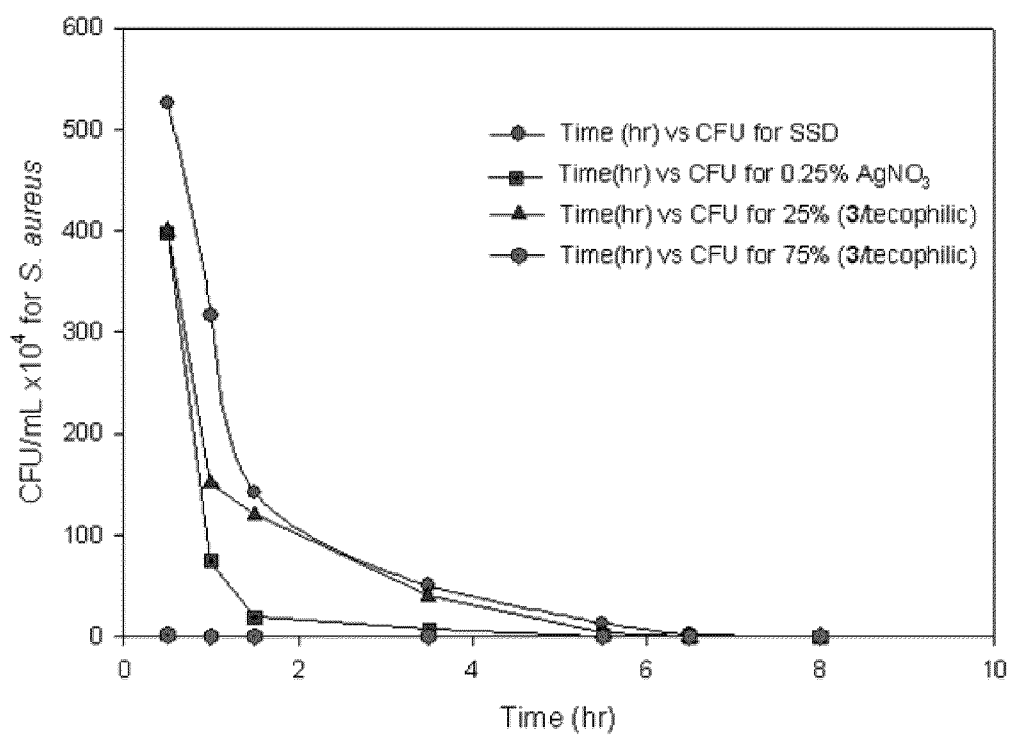
FIG. 29 is a graph showing CFU (colony forming unit) versus time (hours) of the silver compounds on *S. aureus*, expresses the kinetic of the bactericidal activity for each of the silver compounds tested.

Deposition of a few silver particles was observed at the bottom of a test tube when a piece of the fiber mat was placed in 5 mL of distilled water and exposed to light for 4 days. The leaching of the silver particles from the fiber mat surfaces to the solution occurred gradually over time. The release of nano-silver particles from the as-spun mats of complex 106 into an aqueous medium lead to the investigation of the kinetics of kill (bactericidal activity) of the as-spun fiber mat of complex 106 with respect to time by comparing it with silver nitrate and silver sulfadiazine 1% cream or silvadene (SSD), a clinical drug widely in use. Both types of the fiber mat composition 75:25 (amount of Ag=424 μg/mL) and 25:75 (amount of Ag=140 μg/mL) used in this study showed a faster kill rate than SSD (amount of Ag=3020 μg/mL). Silver nitrate (0.5%) with 3176 μg/mL of Ag showed about the same kill rate as complex 106/tecophilic 75:25 (Ag=424 μg/mL) at a silver concentration 8 fold lower than silver nitrate (see FIG. 29). Bactericidal activity of the silver compounds is faster on *P. aeruginosa* than on *S. aureus*. The fiber mats killed bacteria faster and better than silvadene.

The time dependence of the bacteriostatic and bactericidal activities of the as-spun mat of complex 106 as a function of the volume of organism inoculated was examined. The fiber mats of complex 106 showed an effective bactericidal activity on *P. aeruginosa, E. coli* and *S. aureus* for over a week with daily inoculation (25 μL) of freshly grown organism.

This is an indication that the as-spun fiber mat sustained the continuous release of active silver species over a long period of time. Pure Tecophilic® mat as control showed no antimicrobial activity within 24 hours of incubation. The as-spun mat of complex 106 with the 75% complex 106/tecophilic composition showed better bactericidal effect on *P. aeruginosa* than the 25% complex 106/tecophilic for over 2 weeks after inoculating with over 200 μL (2×10$^7$) of freshly grown organism. Bacteriostatic activity was observed for *S. aureus* and *E. coli* after 10 days of the daily streaking of the LB broth solution on an agar plate. Visual inspection of the incubated solutions showed no growth of the organism.

The bactericidal activity of 108, complex 106 and AgNO$_3$ in aqueous LB broth was studied using the minimum inhibitory concentration (MIC) test. There was generally no difference in the bactericidal activity and MIC of complex 106 and AgNO$_3$ after 24 hours of incubation as shown in Table 5. However, after 48 hrs of incubation, silver nitrate showed a better antimicrobial activity at a concentration 2 fold lower than complex 106 (838 μg/mL).

TABLE 5

MIC Result Comparing the Activity of AgNO$_3$ and Complex 106, with both having about the Same Amount of Silver

| Sample ID | Conc. of sample (wt/V %) | Conc. of sample (μg/mL) | Vol. of bacteria (μL) | E. coli (Day) 1 | 2 | P. aereginousa (Day) 1 | 2 | S. aureus (Day) 1 | 2 |
|---|---|---|---|---|---|---|---|---|---|
| AgNO$_3$ | 0.50 | 3462.35 | 100 | − | − | − | − | − | − |
|  | 1DF | 1731.18 |  | − | − | − | − | − | − |
|  | 2DF | 865.59 |  | − | − | − | − | − | − |
|  | 3DF | 432.79 |  | − | − | − | − | − | − |
|  | 4DF | 216.40 |  | − | + | − | − | − | + |
| 106 | 1.38 | 3341.48 | 100 | − | − | − | − | − | − |
|  | 1DF | 1675.74 |  | − | − | − | − | − | − |
|  | 2DF | 837.87 |  | − | − | − | − | − | − |
|  | 3DF | 418.94 |  | − | + | − | + | − | + |
|  | 4DF | 209.47 |  | − | + | − | + | − | + |
| 108 | 0.5 |  | 25 | + |  | + |  | + |  |

MIC result comparing the activity of AgNO$_3$ and 106, with both having about the same amount of silver.
DF is the dilution factor (1 mL);
+ = growth;
− = no growth.
The amount of silver (μg) per mL for each compound was calculated as (molecular mass of Ag/formula wt of compound) × wt %.

The MIC value was not determined for silver sulfadiazine because of the cloudy nature of the solution, and the concentration of 108 used showed no antimicrobial activity. The dilutions with the least concentration of complex 106 (209 μg/mL) and AgNO$_3$ (216 μg/mL) in the MIC test was observed to show growth of the same number of colonies of S. aureus on an agar plate after 24 hours of incubation. The 25% complex 106/tecophilic fiber mat has the least concentration of Ag, 140 μg/mL (see Table 6), and sustain the release of active silver species that were bio-available for days. No growth of the organism was observed with the daily increase in the volume of inocula.

TABLE 6

Showing Details of Silver Compounds used for the Kinetic Studies

| Sample ID | Wt of Ag compds. used (mg) | Volume of LB Broth (ml) | Amount of Ag in sample (mg) | μg of Ag/mL |
|---|---|---|---|---|
| SSD | 20.00 | 5.00 | 6.05 | 1210.00 |
| AgNO$_3$ | 12.80 | 5.00 | 8.13 | 1626.00 |
| AgNO$_3$ | 25.00 | 5.00 | 15.90 | 3176.00 |
| 106/Tecophilic (25:75) | 11.30 | 5.00 | 0.73 | 146.00 |
| 106/Tecophilic (75:25) | 11.40 | 5.00 | 2.21 | 441.00 |

SSD: silver sulfadiazine 1% cream

Thus, the antimicrobial activity of complex 106 was enhanced for a longer period, at a very low concentration of Ag particles by encapsulation in a suitable polymeric fiber. The bactericidal activity of the fiber mat 75% (complex 106/tecophilic) with 424 μg/mL of silver is 8 fold lower in the concentration of Ag than AgNO$_3$ (3176 μg/mL) and showed not only a kill rate as fast as silver nitrate, but also retained the original color of the LB broth, a clear yellow solution unlike silver nitrate which stains and changed the LB broth color to dark brown. The silver-sulfadiazine cream did not readily dissolve in the aqueous LB broth, thus affecting the rate of its bactericidal activity.

Figures 30A, 30B:
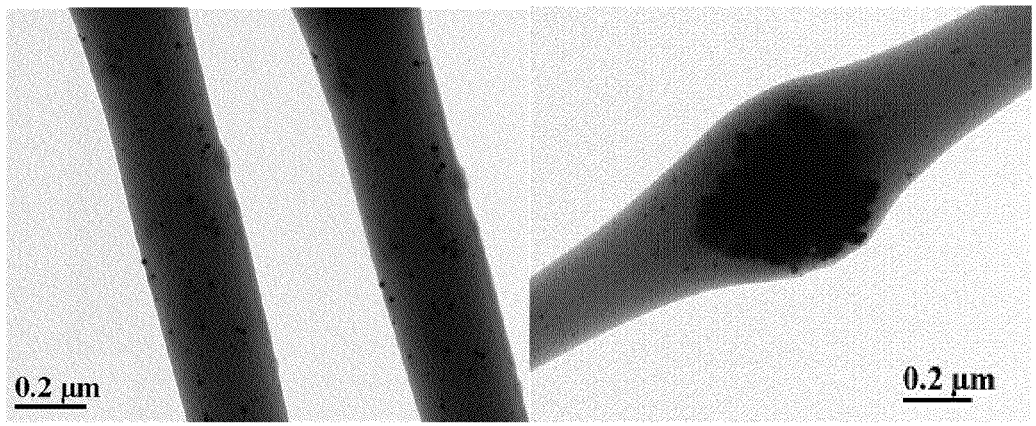
FIGS. 30*a*, 30*b*, 30*c* and 30*d* are images of electrospun fibers from Complex 106 and Tecophilic® (weight ratio 75:25) after two weeks of antimicrobial activity in LB broth media, with FIG. 30*a* being a stereo image of a segment of fiber, FIG. 30*b* being an image of large aggregate (400 nm) silver particles encapsulated in Tecophilic® fiber, FIG. 30*c* being an image of silver aggregates (200 nm to 300 nm in diameter) and silver particles (10 nm to 20 nm in diameter) in a Tecophilic® matrix, and FIG. 30*d* being a top view of a fiber mat with aggregates of silver particles.
Figures 30C, 30D:
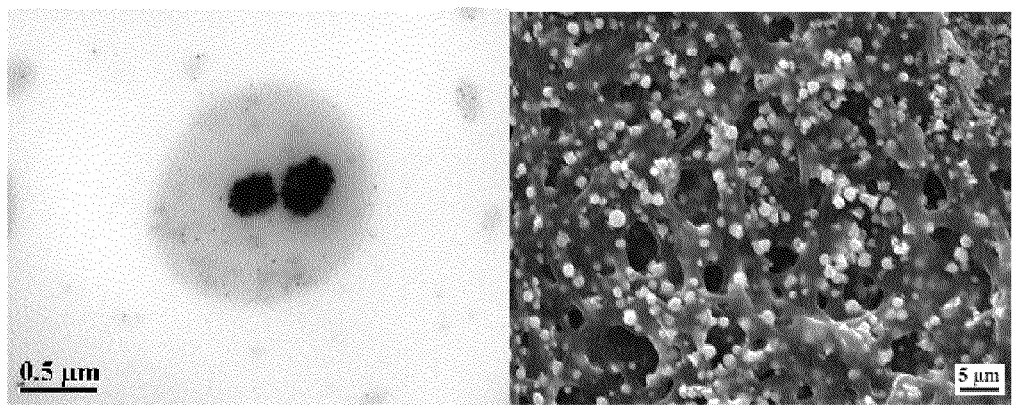

The antimicrobial activity of the fiber mat encapsulating complex 106 can be considered to be a combination of active silver species, which may include AgCl$_2^-$ ions, clusters of Ag$^+$ ions, AgCl and free Ag$^+$ ions. Theoretically, the slow release of the active silver particles in the solution leads to the quick formation of silver chloride. The presence of more chloride anion as the major counter ion will further result in the formation of negatively charged $[Ag_yCl_x]^{n-}$ ion species (where y=1, 2, 3 ... etc; x=2, 3 ... (y+1); n=x−1). The anionic silver complexes of the type $[AgI_3]^{2-}$, $[Ag_2I_4]^{2-}$, $[Ag_4I_8]^{4-}$ and $[Ag_4I_6]^{2-}$ have been formed. The formation of anionic silver chloride species may not be limited to the leached aggregates of silver particles in the solution, but may also be found on the surface of the fiber mats as shown in the SEM images of FIG. 30. Anionic silver dichloride is known to be soluble in an aqueous media and thus will be bio-available. It has been reported that anionic silver halides are toxic to both sensitive and resistance strain bacteria. The adsorbed active silver species on the network of fibers in the mat is an advantage the fiber mat has to increase the surface area of the active silver species over the conventional use of aqueous silver ions. This mechanism might have accounted for the effective bactericidal activity of the fiber mat in an aqueous media, even at such a low concentration of silver compared to the un-encapsulated form of complex 106. Although complex 106 is sparingly soluble in water, its quick decomposition has been observed to occur in aqueous media. Thus, the bactericidal activity of complex 106 is reduced due to poor availability of active silver species in the LB broth media, which might be due to the formation of secondary silver compound especially AgCl.

Acute Toxicity Assessment:

The LD 50 assessment was done by intravenous administration of 108, dissolved in a buffered saline solution, via the tail of rats. Adult rats were used with an average weight of 500 grams. Progressive administration of 0.3 mL of the dose (5 mg, 50 mg) was done weekly. The rats were carefully examined for the dose-response effect. Death occurred 10 minutes after administrating 50 mg of 108, when 50% of the rats showed powerful convulsion before death. Autopsy report showed pulmonary hemorrhage and hemorrhage in the brain of the dead rats, a diagnosis of stroke. The surviving rats were observed to lose weight, with a drastic loss in appetite, and low urine out put. The LD 50 assessment was found to be 100 mg/Kg of rat.

The synthesis of 108 with functionalized groups aids in tailoring the encapsulation of the silver(I) imidazole cyclophane gem diol into a nanofiber. The fiber mat has been shown to have improved the antimicrobial activity of the silver(I)-n-heterocyclic carbene complexes on the inoculum, with a faster kill rate than silvadene in an LB broth medium at a concentration 8 fold lower than silvadene. The encapsulation of the silver N-heterocyclic carbene complexes increases the bio-availability of active silver species and also reduces the amount of silver used. Encapsulated silver(I) carbene complexes in nano-fibers has been demonstrated to be a promising material for sustained and effective delivery of silver ions over a longer period of time with maximum bactericidal activity than supplying silver in an aqueous form. The amount of silver required for antimicrobial activity is reduced with this technique of encapsulation compared to the un-encapsulated form, which often is related to the amount of silver in 0.5% silver nitrate. Furthermore, the ability of the fiber mat to retain the original color of the LB broth is a major cosmetic plus. The assessment of the acute toxicity of the ligand on rats showed an LD50 of 100 mg/Kg of rat, a value considered to be moderately toxic.

In addition to useful antimicrobial, or antibacterial, properties, it is believed that the present invention can inhibit fungal growth, and also viral growth. The compositions of matter and methods of the present invention also contemplate delivery of silver to locations via any known vehicle, including, but not limited to, inhalation through the lungs, direct application of a liquid to an eye, and direct application to a urinary bladder infection, or any other type of topical application.

General Experimental:

Silver (I) oxide, silver sulfadiazine and 1,3-dichloroacetone where purchased from Aldrich. Acetone, acetonitrile, methanol, ethanol, ammonium hexafluorophosphate, and organisms; S. cerevisiae (ATCC 2601), C. albicans (ATCC 10231), A. niger(ATCC 16404), E. coli (ATCC 8739), P. aeruginosa (ATCC 9027), S. aureus (ATCC 6538) were purchased from Fisher. All reagents were used without further purification. Infrared spectra were recorded on Nicolet Nexus 870 FT-IR spectrometer. The $^1$H and $^{13}$C NMR data was recorded on a Varian Gemini 300 MHz instrument, and the spectra obtained were referenced to the deuterated solvents. Mass spectroscopy data were recorded on an ESI-QIT Esquire-LC with a positive ion polarity. The TEM images were recorded on FEI TE CNAI-12 transmission electron microscope (TEM) at 120 KV.

Synthesis of the Imidazolium Cyclophane Gem-Diol Dichloride:

A solution containing 0.24 grams (1.0 mmol) of 2,6-bis(imidazolemethyl)pyridine and 0.254 grams (2.0 mmol) 1,3-dichloroacetone in 60 mL of acetonitrile was stirred at 75° C. for 8 hours to obtain 108 as a brown solid on filtration. The yield is 0.9 mmol at a rate of 89.6%. Colorless crystals of the $PF_6$ salt of 108 were obtained by slow evaporation from acetonitrile/water. The melting point is 175 to 178° C. $^1$H NMR (300 MHz, DMSO-$d_6$): δ 4.68 (s, 4H, $CH_2C(OH)_2C$ $H_2$), 5.67 (s, 4H, $CH_2$), 7.40, (s, 2H, NC(H)CH), 7.47 (d, 2H, J=7.8 Hz, m-pyr), 7.65 (s, 2H, C(OH), 7.89 (s, 2H, NCHC(H)), 7.94 (t, 1H, J=7.8 Hz, p-pyr), 9.34 (s, 2H, NC(H)N). $^{13}$C NMR (75 MHz, DMSO-$d_6$): δ 51.8, 55.2, 91.1, 120.5, 122.0, 123.9, 138.0, 138.8, 152.6. ESI-MS m/z: 384 [$M^{2+}$2Cl$^-$], 348 [$M^{2+}$Cl$^-$]. FTIR (Nujol, cm$^{-1}$): 3387, 3105, 1597, 1564, 1439, 1346, 1171, 1085, 996, 755. Anal. Calcd: C, 48.54; H, 4.41; N, 16.94; Cl, 17.13. Found: C, 48.33; H, 4.32; N, 16.71; Cl, 16.76.

Synthesis of the Dinuclear Silver Carbene Cyclophane Gem-Diol Hydroxide:

The combination of 0.232 grams (1.0 mmol) silver (I) oxide and 0.366 grams (0.9 mmol) of 108 in 70 mL methanol was stirred at room temperature for 50 minutes. The filtrate was concentrated to obtain complex 106 as a yellow solid. Single crystals of complex 106 were obtained from ethanol, containing a spike of carbonate, by slow diffusion.

Yield: 0.618 grams, 0.738 mmol, 82%. The melting point is 202 to 204° C. ESI-MS m/z: 400[$0.5M^{2+}$], 801[$2M^+$], 837 [$2M^+2OH^-$]. FTIR (Nujol, cm$^{-1}$): 3415, 3105, 1596, 1564, 1439, 1344, 1169, 1084, 1028, 996, 758. $^{13}$C NMR (75 MHz, DMSO-$d_6$): δ 48.6, 51.1, 53.8, 92.1, 119.9 (J=1.4 Hz), 121.6, 128.6, 137.8 (J=2.4 Hz), 154.2, 184.9 (Jcarbene-Ag=211 Hz). Anal. Calcd: Ag, 24.54; C, 43.79; H, 4.20; N, 15.24. Found: C, 43.15; H, 4.22; N, 14.89.

Electrospun Fiber:

Tecophilic® was dissolved in a mixture of ethanol and tetrahydrofuran at a ratio of 9 to 1. A solution of complex 106 in ethanol was mixed with a pre-made solution of Tecophilic®. Solutions with different weight ratios between complex 106 and Tecophilic® were prepared. The ratios were 0/100, 25/75 and 75/25. The solutions of complex 106 and Tecophilic® were held in a pipette. An electrical potential difference of 15 KV was applied between the surfaces of the solution drop to the grounded collector, a distance of about 20 cm. Transmission electron microscopy (TEM) and scanning electron microscopy (SEM) were used to characterize the as-spun fibers and fibers exposed to water.

Antimicrobial Test:

Sterilized LB Broth was measured (5 mL) into a sterile tube. A loopful of stationary phase cultured microorganism (E. coli, P. aeruginosa, S. aureus) was introduced into the tube containing the LB Broth solution. The mixture was cultured overnight, at 35° C. in a shaking incubator. The same procedure was done with stationary phased cultured fungi (C. albican, S. cerevisae, A. niger) and incubated without shaking at room temperature for 72 hours.

Fiber Mat Testing:

A constant volume (25 μL) of the freshly grown organism was placed on an LB agar plate and grown to obtain a lawn of the organism. A fiber mat (2.0 cm×2.0 cm) of complex 106 and pure Tecophilic was placed on a lawn of bacteria (E. coli, P. aeruginosa, S. aureus) of an LB agar plate and incubated overnight at 35° C. The bactericidal activity was observed by visual inspection of growth and no growth in and around the area of the fiber mat. About the same dimension of the fiber mat was placed on a lawn of fungi (C. albicans, S. cerevisiae, A. niger) and incubated at room temperature for 48 hours. The diameter of the clear zone was measured.

Minimum Inhibitory Concentration (MIC) Test:

Serial dilutions were made to obtain a range of concentrations by transferring 1 mL of freshly prepared stock solution of the silver compounds (with the same amount of silver particles) into a sterile culture tube containing 2 mL of LB broth, marked A. 1 mL of well mixed solution of A was transferred to culture tube B containing LB broth. The same procedure was repeated to obtain the dilute solution for tube C, D and E. The MIC was determined by visual inspection of growth/no-growth of the above concentrations of the silver compounds marked A-E inoculated with 25 μL of the organisms. After incubation at 35° C. overnight with no growth of organism, an additional 80 μL of freshly grown organisms was added to each of the culture on the second day and incubated at the same temperature.

Kinetic Test of Bactericidal Activity:

Equal volume (5 mL) of LB broth were measured into sterile culture tubes and inoculated with 100 μL of *S. aureus* to each tube containing silver nitrate (12.8 mg, 25 mg), silver sulfadiazine (20 mg), 11.3 mg complex 106/Tecophilic (25:75) and 11.4 mg complex 106/Tecophilic (75:25) fiber mats. The mixtures were incubated at 35° C. and the bactericidal activity was checked over a range of time by streaking one loopful of each mixture on an agar plate. The agar plate was then incubated at 37° C. overnight and the numbers of colonies of organism formed counted. The same procedure was repeated using 100 μL *P. aeruginosa*.

Animal Studies:

Male Sprague Dawley available from Harlan Sprague Dawley (Indianapolis, Ind.) adult rats (400 to 500 grams body weight) were housed in the university of Akron animal facility. Temperature and humidity were held constant, and the light/dark cycle was 6.00 am-6.00 pm: light, 6.00 pm-6.00 am: dark. Food available from Lab diet 5P00, Prolab, PMI nutrition, Intl. (Bretwood, Mo.) and water were provided ad libitum. Animals were anesthetized with ether in order to inject the compound into the tail vein, using a 27 gauge syringe needle in a volume of 0.3 mL sterile saline. The dosages for the ligand were 5 mg and 50 mg. At the end dosages of the experiment, animals were terminated and the liver, lung, kidney and heart tissues were removed and frozen at −70° C. Urine samples were collected daily for later examination of the compound distribution. These studies were approved by the University of Akron Institutional Animal Care and Use Committee (IACUC).

X-ray Crystallographic Structure Determination:

Crystal data and structure refinement parameters contained in the supporting information. Crystals of 108 and complex 106 were each coated in paraffin oil, mounted on kyro loop, and placed on a goniometer under a stream of nitrogen. X-ray data were collected at a temperature of 100 K on a Brucker Apex CCD diffractometer using Mo Kα radiation (λ=0.71073 Angstroms). Intensity data were integrated using SAINT software, and an empirical absorption correction was applied using SADABS. Structures 108 and complex 106 were solved by direct methods and refined using full-matrix least square procedures. All non-hydrogen atoms were refined with anisotropic displacement.

Additional Embodiments:

In another embodiment, the present invention relates to metal complexes of N-heterocyclic carbenes that contain an anti-fungal and/or anti-microbial moiety and/or group in combination with one or more additional active moieties and/or groups selected from fluoroquinolone compounds or derivatives thereof; steroids or derivatives thereof; anti-inflammatory compounds or derivatives thereof; anti-fungal compounds or derivatives thereof; anti-bacterial compounds or derivatives thereof; antagonist compounds or derivatives thereof; $H_2$ receptor compounds or derivatives thereof; chemotherapy compounds or derivatives thereof; tumor suppressor compounds or derivatives thereof; or $C_1$ to $C_{16}$ alkyl heteroatom groups where the heteroatom is selected from S, O, or N. In still another embodiment, the present invention relates to metal complexes of N-heterocyclic carbenes that contain an anti-fungal and/or anti-microbial moiety and/or group in combination with two or more additional active moieties and/or groups selected from fluoroquinolone compounds or derivatives thereof; steroids or derivatives thereof; anti-inflammatory compounds or derivatives thereof; anti-fungal compounds or derivatives thereof; anti-bacterial compounds or derivatives thereof; antagonist compounds or derivatives thereof; $H_2$ receptor compounds or derivatives thereof; chemotherapy compounds or derivatives thereof; tumor suppressor compounds or derivatives thereof; or $C_1$ to $C_{16}$ alkyl heteroatom groups where the heterotatom is selected from S, O, or N.

Such double, triple or higher action compounds can be represented by the compounds represented by Formulas 301 to 305 shown below:

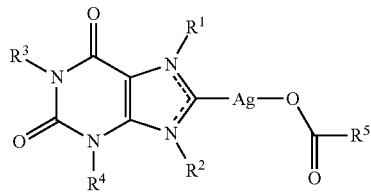

301

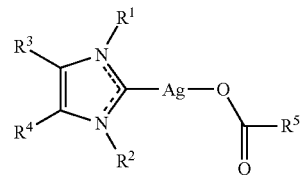

302

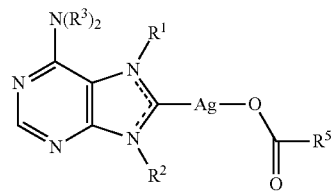

303

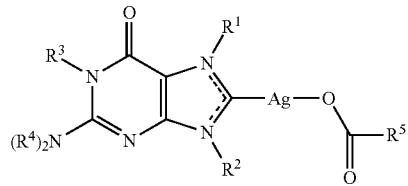

304

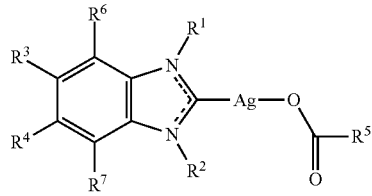

305 where $R^1$, $R^2$, $R^3$, $R^4$, $R^6$ and $R^7$, if present, are each independently selected from hydrogen; hydroxy; $C_1$ to $C_{12}$ alkyl; $C_1$ to $C_{12}$ substituted alkyl; $C_3$ to $C_{12}$ cycloalkyl; $C_3$ to $C_{12}$ substituted cycloalkyl; $C_2$ to $C_{12}$ alkenyl; $C_3$ to $C_{12}$ cycloalkenyl; $C_3$ to $C_{12}$ substituted cycloalkenyl; $C_2$ to $C_{12}$ alkynyl; $C_6$ to $C_{12}$ aryl; $C_5$ to $C_{12}$ substituted aryl; $C_6$ to $C_{12}$ arylalkyl; $C_6$ to $C_{12}$ alkylaryl; $C_3$ to $C_{12}$ heterocyclic; $C_3$ to $C_{12}$ substituted heterocyclic; $C_1$ to $C_{12}$ alkoxy; $C_1$ to $C_{12}$ alcohols; $C_1$ to $C_{12}$ carboxy; biphenyl; $C_1$ to $C_6$ alkyl biphenyl; $C_2$ to $C_6$ alkenyl biphenyl; or $C_2$ to $C_6$ alkynyl biphenyl, and where $R^5$ is selected from fluoroquinolone compounds or derivatives thereof; steroids or derivatives thereof; anti-inflammatory compounds or derivatives thereof; anti-fungal compounds or derivatives thereof; anti-bacterial compounds or derivatives thereof; antagonist compounds or derivatives thereof; $H_2$ receptor compounds or derivatives thereof; chemotherapy compounds or derivatives thereof; tumor suppressor compounds or derivatives thereof; or $C_1$ to $C_{16}$ alkyl heteroatom groups where the heterotatom is selected from S, O, or N.

In another embodiment, the compounds of the present invention are "triple action" compounds due to the inclusion of two active substituent groups selected from fluoroquinolone compounds or derivatives thereof; steroids or derivatives thereof; anti-inflammatory compounds or derivatives thereof; anti-fungal compounds or derivatives thereof; anti-bacterial compounds or derivatives thereof; antagonist, compounds or derivatives thereof; $H_2$ receptor compounds or derivatives thereof; chemotherapy compounds or derivatives thereof; tumor suppressor compounds or derivatives thereof; or $C_1$ to $C_{16}$ alkyl heteroatom groups where the heterotatom is selected from S, O, or N. In this embodiment one of $R^1$, $R^2$, $R^3$, $R^4$, $R^6$ or $R^7$ is selected from fluoroquinolone compounds or derivatives thereof; steroids or derivatives thereof; anti-inflammatory compounds or derivatives thereof; anti-fungal compounds or derivatives thereof; anti-bacterial compounds or derivatives thereof; antagonist compounds or derivatives thereof; $H_2$ receptor compounds or derivatives thereof; chemotherapy compounds or derivatives thereof; tumor suppressor compounds or derivatives thereof; or $C_1$ to $C_{16}$ alkyl heteroatom groups where the heterotatom is selected from S, O, or N, where the remaining $R^1$, $R^2$, $R^3$, $R^4$, $R^6$ and $R^7$ groups are each independently selected from hydrogen; hydroxy; $C_1$ to $C_{12}$ alkyl; $C_1$ to $C_{12}$ substituted alkyl; $C_3$ to $C_{12}$ cycloalkyl; $C_3$ to $C_{12}$ substituted cycloalkyl; $C_2$ to $C_{12}$ alkenyl; $C_3$ to $C_{12}$ cycloalkenyl; $C_3$ to $C_{12}$ substituted cycloalkenyl; $C_2$ to $C_{12}$ alkynyl; $C_6$ to $C_{12}$ aryl; $C_5$ to $C_{12}$ substituted aryl; $C_6$ to $C_{12}$ arylalkyl; $C_6$ to $C_{12}$ alkylaryl; $C_3$ to $C_{12}$ heterocyclic; $C_3$ to $C_{12}$ substituted heterocyclic; $C_1$ to $C_{12}$ alkoxy; $C_1$ to $C_{12}$ alcohols; $C_1$ to $C_{12}$ carboxy; biphenyl; $C_1$ to $C_6$ alkyl biphenyl; $C_2$ to $C_6$ alkenyl biphenyl; or $C_2$ to $C_6$ alkynyl biphenyl, and where $R^5$ is selected from fluoroquinolone compounds or derivatives thereof; steroids or derivatives thereof; anti-inflammatory compounds or derivatives thereof; anti-fungal compounds or derivatives thereof; anti-bacterial compounds or derivatives thereof; antagonist compounds or derivatives thereof; $H_2$ receptor compounds or derivatives thereof; chemotherapy compounds or derivatives thereof; tumor suppressor compounds or derivatives thereof; or $C_1$ to $C_{16}$ alkyl heteroatom groups where the heterotatom is selected from S, O, or N. In this embodiment, the two active substituent groups attached to Compounds 301 through 305 should not be the same.

In one embodiment, the one or more double, triple or high action compounds of the present invention can contain one or more additional active groups, or moieties, as defined above that are bound directly to one or more points of the metal complexes of N-heterocyclic carbenes disclosed herein. In this embodiment, no intervening linking group, or groups, are needed. In another embodiment, suitable linking groups can be utilized to bind the one or more additional active groups, or moieties, to one or more points of the metal complexes of N-heterocyclic carbenes disclosed herein. Suitable linking groups are known in the art and as such a discussion thereof is omitted for the sake of brevity.

Figure 31:
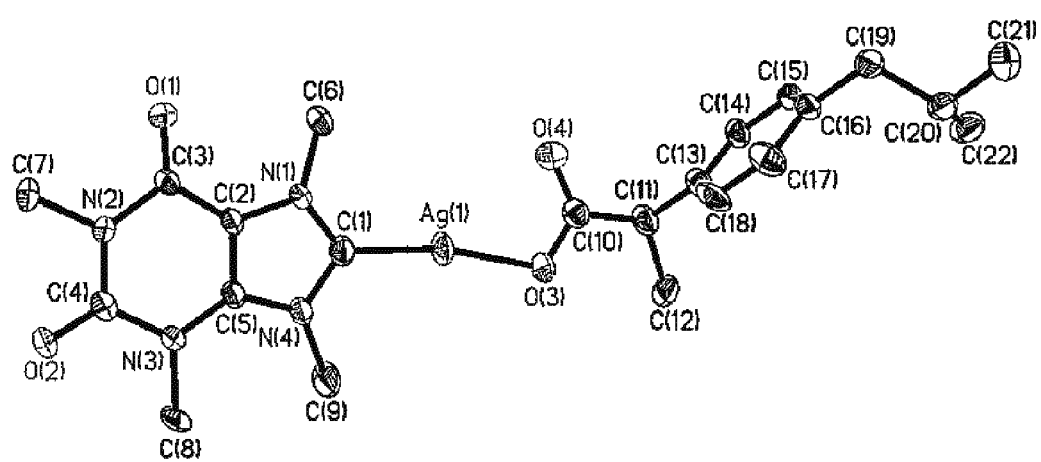
FIG. 31 is a thermal ellipsoid plot of an N-heterocyclic carbene compound according to another embodiment of the present invention.

One example of one of the above compounds is shown in FIG. 31 a multifunctional SCC of Formula 301 where $R^1$ through $R^4$ are comprised of methyl groups and the $R^5$ carboxylate is ibuprofen. The synthesis of SCCI IBU is achieved by using one equivalent of 1,3,7,9-tetramethylxanthinium iodide and two equivalents of silver (I) ibuprofen salt were stirred in methanol. After 1.5 hours a yellow precipitate was filtered from the reaction mixture through Celite®. The filtrate was collected and volatiles removed via rotary evaporation. The crude solid was stirred in diethyl ether to afford SCCI IBU as a white solid.

TABLE 7

Efficacy Data

| Bacterial species Isolate | Formula 301 $R^5$ = $CH_3$ SCC1 (μg/ml) | | Formula 301 $R^5$ = ibuprofen SCC1-IBU (μg/ml) | | Tobramycin (μg/ml) | |
|---|---|---|---|---|---|---|
| | MIC | MBC | MIC | MBC | MIC | MBC |
| *Pseudomonas aeruginosa* | | | | | | |
| PA 01-V | 1 | 2 | 2 | 6 | 15 | >20 |
| PA M57-15 | 2 | 4 | 1 | 2 | 0.5 | 1 |
| PA RR05 | 0.5 | 1 | 0.25 | 2 | 0.5 | 1 |
| PA HP3 | 4 | 8 | 0.25 | 2 | 4 | 8 |
| PA LF05 | 1 | 1 | 1 | 1 | 0.5 | 1 |
| *Alcaligenes xylosoxidans* | | | | | | |
| AX 22 | 0.5 | 2 | 0.5 | 2 | 20 | >20 |
| AX RE05 | 4 | 8 | 1 | 2 | >20 | >20 |
| *Stenotrophomonas maltophilia* | | | | | | |
| SM AH08 | 4 | 8 | 1 | 2 | 8 | 20 |
| Methicillin resistant *Staphylococcus aureus* (MRSA) | | | | | | |
| SA LL06 | 8 | 10 | 2 | 6 | >20 | >20 |
| SA EH06 | 6 | 20 | 2 | 4 | >20 | >20 |
| *Yersinia pestis* | | | | | | |
| YP1-1CO92-LCR- | 0.5 | 1 | 0.5 | 2 | 0.25 | 0.25 |
| *Escherichia coli* | | | | | | |
| J53 | 1 | 1 | 0.5 | 0.5 | 1 | 1 |
| J53 + pMG101 | >20 | >20 | >20 | >20 | 1 | 1 |

It should be evident that the present invention is highly effective in providing a method of inhibiting microbial growth by administration of a N-functionalized silver carbene complex. It is, therefore, to be understood that any variations evident fall within the scope of the claimed invention and thus, the selection of specific component elements can be determined without departing from the spirit of the invention herein disclosed and described.

What is claimed is:

1. A method for treating a bacterial infection comprising the step of administering to a patient in need thereof a therapeutically effective amount of a compound selected from the group consisting of

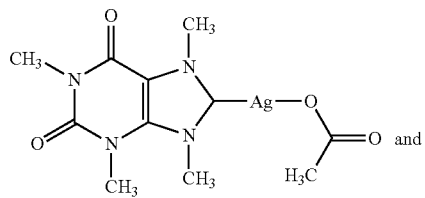 and

-continued
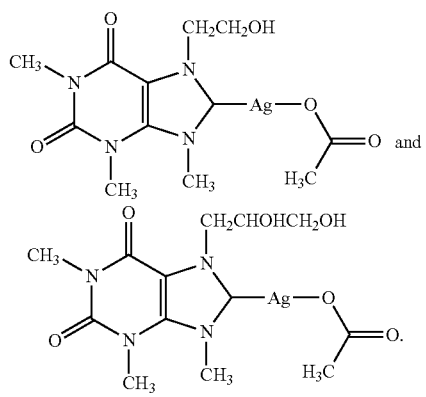
and
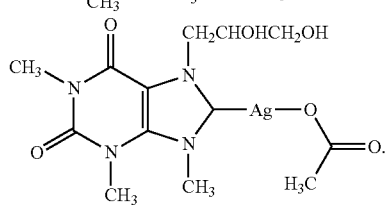
* * * * *